United States Patent [19]

Ginsberg et al.

[11] Patent Number: 5,306,620
[45] Date of Patent: Apr. 26, 1994

[54] ANTIBODIES THAT BIND TO A LIGAND-INDUCED BINDING SITE ON INTEGRIN AND INDUCE INTEGRIN ACTIVATION

[75] Inventors: Mark H. Ginsberg; Timothy E. O'Toole; Edward F. Plow, all of San Diego, Calif.; Andrew L. Frelinger, III, Natick, Mass.

[73] Assignee: The Scripps Research Institute, La Jolla, Calif.

[21] Appl. No.: 613,357

[22] Filed: Nov. 13, 1990

Related U.S. Application Data

[63] Continuation-in-part of Ser. No. 417,565, Oct. 5, 1989, Pat. No. 5,284,751, which is a continuation-in-part of Ser. No. 175,342, Mar. 31, 1988, Pat. No. 5,114,842, which is a continuation-in-part of Ser. No. 70,953, Jul. 8, 1987, abandoned.

[51] Int. Cl.$^5$ .......................................... G01N 33/567
[52] U.S. Cl. ................................. 435/7.21; 436/63; 436/548; 436/811
[58] Field of Search ................. 435/7.21; 436/63, 501, 436/548, 811

[56] References Cited

U.S. PATENT DOCUMENTS 5,114,842  5/1992  Plow et al. ........................ 424/85.8

OTHER PUBLICATIONS

Kouns et al., J. Biol. Chem. 265:20594–20601, 1990.
Frelinger et al., J. Biol. Chem 263:12397–12402, 1988.
Jennings et al., Blood 65:1112–1119, 1985.
Frelinger, et al., J. Cell Biol. 107: 386a, abst. No. 2199 (1988).
Frelinger et al., J. Biol. Chem. 265: 6346–6352 (1990).
Ginsberg et al., J. Biol. Chem. 262: 5437–5440 (1987).
Shadle et al., J. Cell. Biol. 99: 2056–2060 (1984).
Ginsberg et al., J. Clin. Invest. 78: 1103–1111 (1986).
Shattil et al., J. Biol. Chem. 260: 11107–11114 (1985).
Shattil et al., J. Biol. Chem. 262: 992–1000 (1987).
Coller, B. S., J. Cell Biol. 103: 451–456 (1986).
D'Souza et al., J. Biol. Chem. 265: 3440 (1990).
Wright et al., J. Immunol. 136: 1759–1764 (1986).
Detmers et al., J. Cell Biol. 105: 1137–1145 (1987).
Altieri et al., J. Cell. Biol. 107: 1893–1900 (1988).
Phillips et al., J. Clin. Invest. 82:495–501 (1988).
Buyon et al., J. Immunol. 140: 3156–3160 (1988).

Primary Examiner—Esther L. Kepplinger
Assistant Examiner—Donna C. Wortman
Attorney, Agent, or Firm—Douglas A. Bingham; Thomas Fitting; April C. Logan

[57] ABSTRACT

An integrin-activating antibody is disclosed that immunoreacts with an integrin and when immunoreacted increases the binding affinity of the integrin for binding to ligands specific for the integrin. The antibody also immunoreacts with a ligand-induced binding site (LIBS) on the integrin when the integrin is specifically bound to its ligand. Further disclosed are therapeutic compositions and methods for promoting cell adhesion using the disclosed integrin-activating antibodies.

4 Claims, 4 Drawing Sheets

ANTIBODIES THAT BIND TO A LIGAND-INDUCED BINDING SITE ON INTEGRIN AND INDUCE INTEGRIN ACTIVATION

CROSS REFERENCE TO RELATED APPLICATION

This is a continuation-in-part application of copending application Ser. No. 417,565, filed Oct. 5, 1989, now U.S. Pat. No. 5,284,751, which is a continuation-in-part application of copending application Ser. No. 175,342, Pat. No. 5,114,842, filed Mar. 31, 1988, which is a continuation-in-part application of copending application Ser. No. 070,953, abandoned, filed Jul. 8, 1987, the disclosures of which are hereby incorporated by reference.

TECHNICAL FIELD

The present invention relates to antibodies that activate integrins by binding the integrin and increasing the affinity of the integrin for its ligand. The antibodies also immunoreact with a ligand-induced binding site that is produced when a cell adhesion receptor specifically binds to a peptide, polypeptide or protein ligand. The present invention also relates to therapeutic methods to increase cell adhesion mediated by activated integrins, particularly platelet and endothelial cell adhesion.

BACKGROUND

Cell adhesion generally involves recognition of specific adhesive proteins by cell surface receptors. A family of cell surface receptors of particular interest to the present invention are the integrins.

Integrins are a functionally and structurally related group of cell adhesion receptors that interact with a wide variety of ligands including extracellular matrix glycoproteins, complement and other cells. Hynes, *Cell*, 48:549-554 (1987); Ginsberg et al., *Thromb. Haemostas.*, 59:1-6 (1988); and Ruoslahti et al., *Science*, 238:491-497 (1987). Integrins participate in cell-matrix and cell-cell adhesion in many physiologically important processes including embryological development, hemostasis, thrombosis, wound healing, phagocytosis, immune and nonimmune defense mechanisms and oncogenic transformation. Two human genetic diseases, Glanzmann'-thrombasthenia and leukocyte adhesion deficiency, involve members of the integrin family.

Because of the vital role integrins play in cellular processes, the regulation of integrin function has important biological consequences. One approach to regulating integrin function is by modulating the affinity of the integrin for its ligand. Some members of the integrin family have been shown to require activation to manifest full competence to bind their ligand. See, for example, Wright et al., *J. Immunol.*, 136:1759-1764 (1986) and Detmers et al., *J. Cell Biol.*, 105:1137-1145 (1987) for complement receptor; and see Bennett et al., *J. Clin. Invest.*, 64:1393-1401 (1979) and Marguerie et al., *J. Biol. Chem.*, 254:5357-5363 (1979) for platelet receptor (GPIIb-IIIa). Modulation of the affinity of an integrin for its ligand is the approach taken by the present invention to regulate integrin function.

Structurally, integrins are heterodimeric complexes comprised of noncovalently associated alpha and beta subunits. Within the integrin family there are recognized groups related by the presence of a similar beta subunit and members within each group are distinguished by unique alpha subunits.

For instance, GPIIb-IIIa is a noncovalent, $Ca^{++}$-dependent, heterodimer complex comprised of alpha and beta subunits. Jennings et al., *J. Biol. Chem.*, 257:10458-10466 (1982). The alpha subunit, GPIIb consists of a heavy chain (hGPIIb) having a relative molecular weight of about 120 kilodaltons (KDa), and a light chain (lGPIIb) of about 20 KDa that are linked together by disulfide bonds. The beta subunit, GPIIIa is a single chain polypeptide of about 100 KDa. Phillips et al., *J. Biol. Chem.*, 252:2121-2126 (1977). Cell surface molecules immunologically related to GPIIb-IIIa have been identified on a variety of cell types. See Thiagarajan et al., *J. Clin. Invest.*, 75:896-901 (1985); Plow et al., *Proc. Natl. Acad. Sci. USA*, 83:6002-6006 (1986); and Fitzgerald et al., *J. Biol. Chem.*, 260:10893-10896 (1985).

GPIIb-IIIa contributes to platelet function through interactions with RGD-containing proteins such as fibrinogen [Bennett et al., *Proc. Natl. Acad. Sci. USA*, 80:2417-2421 (1983)], fibronectin [Ginsberg et al., *J. Clin. Invest.*, 71:619-624 (1983)], and von Willebrand factor [Ruggeri et al., *Proc. Natl. Acad. Sci. USA*, 79:6038-6041 (1982)], and therefore is a component of the common platelet adhesive protein receptor [Pytela et al., *Science*, 231:1559-1562 (1986) and Plow et al., *J. Biol. Chem.*, 259:5388-5391 (1984)].

Recent evidence indicates that GPIIb-IIIa is one of several adhesion receptors that share a similar beta subunit and the functional property of recognizing the tripeptide amino acid residue sequence Arg-Gly-Asp (using single letter symbols, RGD). Pytela et al., *Science*, 231:1559-1562 (1986) and Ruoslahti et al., *Cell*, 44:517-518 (1986). In addition to GPIIb-IIIa, this group of related receptors includes the vitronectin receptor (VnR) and fibronectin receptor (FnR) isolated from osteosarcoma cells [Pytela et al., *Cell*, 40:191-198 (1985), Pytela et al., *Proc. Natl. Acad. Sci. USA*, 82:5766-5770 (1985) and Sanchez-Madrid et al., *J. Exp. Med.*, 158:1785-1803 (1983)].

The similar functional, structural, and antigenic properties of these proteins suggests GPIIb-IIIa and VnR (a $\beta_3$ type GPIIIa-containing receptor) are members of an adhesion receptor group for which the designation "cytoadhesin" has been proposed. Plow et al., *Proc. Natl. Acad. Sci. USA*, 83:6002-6006 (1986). Within the cytoadhesin group, distinct alpha subunits combine with a common or very similar beta subunit, resulting in functionally distinguishable receptors. Ginsberg et al., *J. Biol. Chem.*, 262:5437-5440 (1987).

At least two other groups of heterodimeric adhesion receptors have been identified in which a common beta subunit combines with a number of distinct alpha subunits. One group is found on leukocytes and has been referred to as the leukocyte adhesion family and includes LFA-1, Mac-1, and p150,95. Sanchez-Madrid et al., *J. Exp. Med.*, 158:1785-1803 (1983) and Springer et al., *Ciba. Found. Symp.*, 118:102-126 (1986). The other is more widely distributed and has been referred to as the VLA family Hemler et al., *J. Biol. Chem.*, 262:3300-3309 (1987). The beta subunit of the VLA family [Hemler et al., *J. Biol. Chem.*, 262:3300-3309 (1987)] in the chicken has been cloned and sequenced and designated "Integrin" [Tamkun et al., *Cell*, 46:271-282 (1986)]. The sequence of chicken integrin is similar to that of GPIIIa [Fitzgerald et al., *J. Biol. Chem.*, 262:3936-3939 (1987)] and to the beta subunit of the leukocyte adhesion family [Kishimoto et al., *Cell*, 48:681-690 (1987)]. Moreover, partial sequences of several alpha subunits also indicate similarities. Ginsberg et al., *J. Biol. Chem.*, 262:5437-5440 (1987); Suzuki et al., *Proc. Natl. Acad. Sci. USA*, 83:8614-8618 (1986); and Charo et al., *Proc. Natl. Acad. Sci. USA*, 83:8351-8356 (1986).

The sites on GPIIb-IIIa, or the other cytoadhesins, that are required for their functions as adhesion receptors are not well characterized. Several observations suggest that a functionally significant site on GPIIb-IIIa is near the epitope defined by the monoclonal antibody PMI-1. This antibody binds to the heavy chain of GPIIb [Shadle et al., *J. Cell. Biol.*, 99:2056-2060 (1984)]and defines a region of GPIIb that is associated with several distinct functional activities. First, PMI-1 inhibits adhesion of washed platelets to collagen. Shadle et al., *J. Cell. Biol.*, 99:2056-2060 (1984). Second, the surface orientation of this region is regulated by divalent cations because millimolar (mM) concentrations of calcium or magnesium suppress expression of the PMI-1 epitope. Ginsberg et al., *J. Clin. Invest.*, 78:1103-1111 (1986). Third, abnormal divalent cation regulation of the conformation of this site is associated with a functional thrombasthenic state. Ginsberg et al., *J. Clin. Invest.*, 78:1103-1111 (1986). Fourth, stimulation of platelets with up to 100 micromolar adenosine diphosphate (ADP) or epinephrine, 1 unit per milliliter thrombin, or 50 micrograms per milliliter calf skin collagen does not substantially increase the binding of PMI-1 antibodies to platelets.

Chemical cross-linking studies have localized the ligand-binding site of GPIIb-IIIa to the alpha subunit at a location proximal to the calcium binding site. D'Souza et al., *J. Biol. Chem.*, 265:3440 (1990).

In addition, in the case of certain integrins such as GPIIb-IIIa, the binding of ligand, such as fibrinogen, alters the shape of the receptor resulting in the expression of new antibody-binding sites referred to as ligand-induced binding sites (LIBS). See for example, Frelinger et al., *J. Biol. Chem.*, 263:12397-12402 (1988) and Frelinger et al., *J. Biol. Chem.*, 265:6346-6352 (1990). LIBS were also detected on the vitronectin receptor, suggesting that this property is common to all integrins [Ginsberg et al., *J. Biol. Chem.*, 262:5437-5440 (1987)].

Platelet activation has been reported to produce the appearance of antigenic sites on the platelet surface that are not present in the non-activated platelet, and at least one of such induced sites has been localized to the GPIIb-IIIa receptor complex. Shattil et al, *J. Biol. Chem.* 260:11107-11114 (1985); Coller, B. S., *J. Cell Biol.*, 103:451-456 (1986).

BRIEF SUMMARY OF THE INVENTION

It has now been discovered that a class of antibody can be prepared that activates integrin by immunoreacting with the integrin and increasing the affinity of the integrin for its ligand. This class of integrin-activating antibodies has the additional property of preferentially immunoreacting with an integrin cell surface receptor when the receptor is specifically bound to (occupied by) its ligand as compared to immunoreaction with non-occupied receptor or non-bound ligand. That is, the antibody also immunoreacts with a ligand-induced binding site (LIBS) present on the integrin when specifically bound by ligand.

Thus the invention contemplates an integrin-activating antibody that immunoreacts with an integrin and when immunoreacted increases the binding affinity of the integrin for binding to a ligand specific for said integrin and immunoreacts with a ligand-induced binding site formed on said integrin with enhanced affinity when said integrin is specifically bound to said specific ligand.

Also contemplated is a method for activating an integrin that binds to a specific ligand comprising contacting the integrin with a solution containing an activating amount of an integrin-activating antibody of this invention.

In a related embodiment the invention describes a therapeutic composition for increasing adhesion of cells that express cell surface integrin comprising in a pharmaceutically acceptable vehicle a therapeutically effective amount of the integrin-activating antibodies of this invention.

A related embodiment contemplates a dressing for wound healing comprising a support matrix containing a means for holding and releasing a therapeutic composition, where the means for holding and releasing contains a therapeutically effective amount of a therapeutic composition for increasing platelet cell adhesion comprising in a pharmaceutically acceptable vehicle an integrin-activating antibody of this invention.

A diagnostic method is also described for determining activation competence of cells having cell surface integrin comprising:

(a) admixing said cells in a physiological fluid with an activating amount of integrin-activating antibodies of this invention to form an activating admixture;

(b) maintaining the activating admixture for a time period sufficient for the cell surface integrin to immunoreact with the integrin-activating antibodies and form an activated integrin immunocomplex on the surface of the cells; and (c) assaying for the presence of the activated integrin immunocomplex formed in step (b) and thereby the activation competence of said cell.

BRIEF DESCRIPTION OF THE DRAWINGS

In the Figures forming a portion of the disclosure of this invention.

DETAILED DESCRIPTION OF THE INVENTION

A. Definitions

Figure 1:
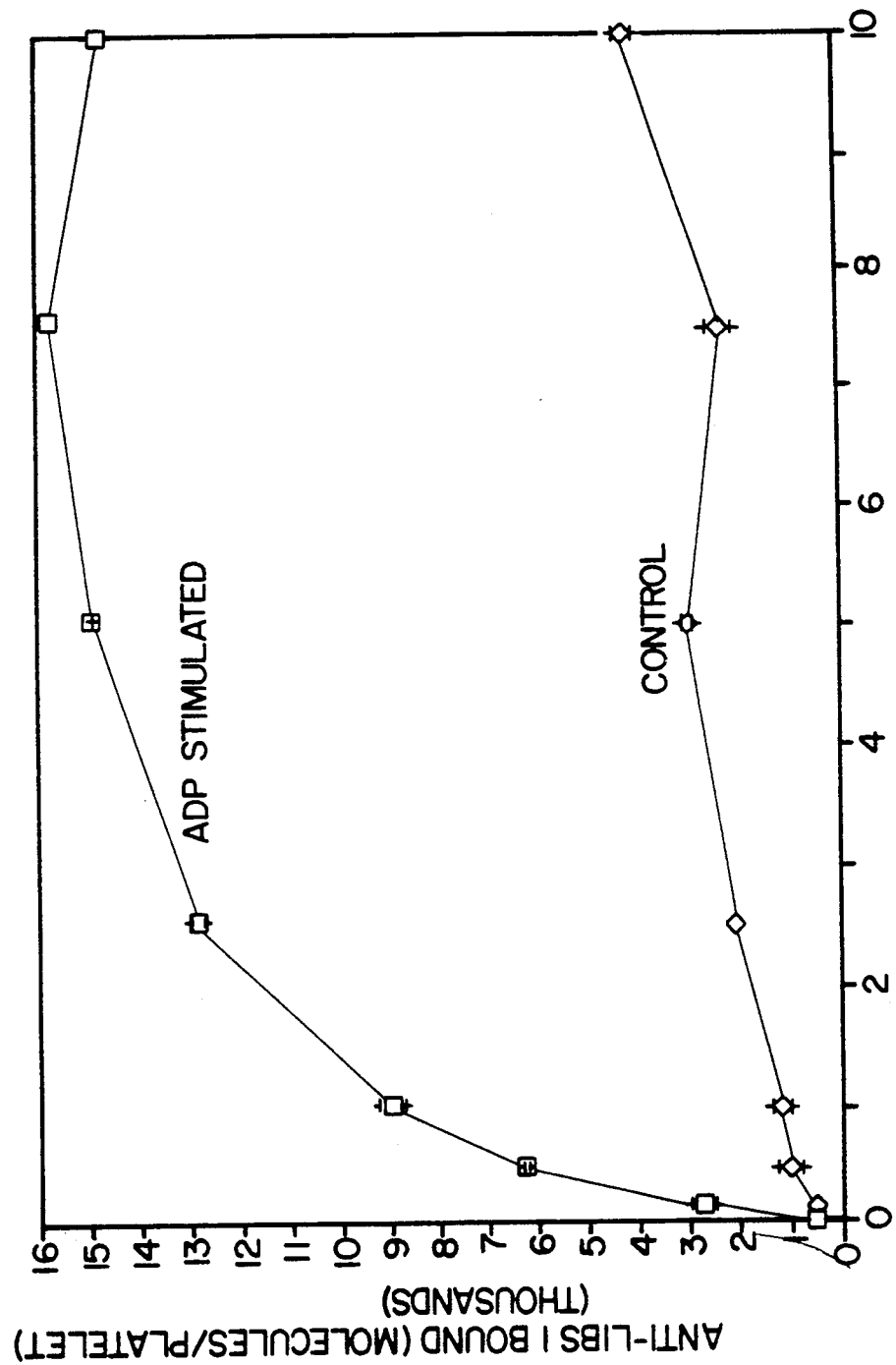
FIG. 1 illustrates anti-LIBS1 binding to platelets in the presence of ADP-stimulated fibrinogen as described in Example 4. Gel-filtered platelets (1 $\times 10^8$ platelets/ml) were incubated with $^{125}$I-labeled anti-LIBS1 and varied concentrations of fibrinogen in the presence (ADP-stimulated) or absence (Control) of ADP (10 uM) for 30 minutes at 37 C. Platelet-bound radioactivity was separated from free by centrifuging the platelets through a layer of sucrose. Results are shown as the average of triplicate determinations +/ − one standard deviation.

Amino Acid: All amino acid residues identified herein are in the natural L-configuration. In keeping with standard polypeptide nomenclature, *J. Biol. Chem.*, 243:3557-59, (1969), abbreviations for amino acid residues are as shown in the following Table of Correspondence:

| TABLE OF CORRESPONDENCE | | |
|---|---|---|
| SYMBOL | | |
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

It should be noted that all amino acid residue sequences are represented herein by formulae whose left to right orientation is in the conventional direction of amino-terminus to carboxy-terminus. Furthermore, it should be noted that a dash at the beginning or end of an amino acid residue sequence indicates a bond to a further sequence of one or more amino acid residues up to a total of about fifty residues in the polypeptide chain.

Polypeptide and Peptide: Polypeptide and peptide are terms used interchangeably herein to designate a linear series of no more than about 50 amino acid residues connected one to the other by peptide bonds between the alpha-amino and carboxy groups of adjacent residues.

Protein: Protein is a term used herein to designate a linear series of greater than 50 amino acid residues connected one to the other as in a polypeptide.

Receptor: Receptor and receptor protein are terms used herein to indicate a biologically active proteinaceous molecule that specifically binds to (or with) other molecules.

Ligand and Cognate Ligand: Ligand refers to a molecule that contains a structural portion that is bound by specific interaction with a particular receptor protein.

Ligand-induced Binding Site (LIBS): A LIBS is a neo-antigenic determinant that is expressed by a cell surface receptor-ligand complex that is produced by a non-random (specific) binding reaction but is not expressed by either the non-occupied receptor or the non-bound ligand. A LIBS can be either "conformational" or "sequential". A LIBS as used herein can be the result of specific alterations of the receptor induced by ligand binding, i.e., a "cryptic antigenic determinant", or it can be formed by a combination of receptor and ligand amino acid residues at a receptor-ligand contact site.

Cryptic Antigenie Determinant: Refers to a neo-antigenic determinant formed by changes in conformation or membrane-surface orientation of a receptor protein upon non-random binding to its cognate (specific) ligand. The receptor proteins described herein do not normally express a cryptic antigenic determinant unless the receptor has specifically bound a ligand.

B. Antibodies and Antibody Compositions

The term "antibody" in its various grammatical forms is used herein to refer to immunoglobulin molecules and immunologically active portions of immunoglobulin molecules, i.e., molecules that contain an antibody combining site or paratope. Illustrative antibody molecules are intact immunoglobulin molecules, substantially intact immunoglobulin molecules and those portions of an immunoglobulin molecule that contain the paratope, including those portions known in the art as Fab, Fab', F(ab')₂ and F(v).

The term "antibody combining site" refers to that structural portion of an antibody molecule comprised of a heavy and light chain variable and hypervariable regions that specifically binds (immunoreacts with) antigen. The term "immunoreact" in its various forms is used herein to refer to binding between an antigenic determinant-containing molecule and a molecule containing an antibody combining site such as a whole antibody molecule or a portion thereof.

The term "antigenic determinant" refers to the actual structural portion of the antigen that is immunologically bound by an antibody combining site. The term is also used interchangeably with "epitope".

As used herein, the term "specifically binds" refers to a non-random binding reaction between two molecules, for example between an antibody molecule immunoreacting with an antigen or between a cell surface integrin receptor and a ligand molecule. Illustrative of a specifically-bound receptor-ligand complex is that between platelet GPIIb-IIIa and fibrinogen at the platelet surface. Other ligands known to specifically bind GPIIb-IIIa and express a LIBS on the receptor-ligand complex includes the polypeptide GRGDSP, the gamma chain polypeptide from amino acid residue 400 to 411 of fibrinogen, and the like.

Other specific binding reactions between an integrin and a specific ligand are well known and depend upon the particular integrin and the ligandbinding specificity of the integrin as described further herein.

The ligand to which an integrin specifically binds is referred to as a specific ligand, and must necessarily be recited in the context of a particular integrin. Specific ligands for binding to integrins are well characterized for many integrins described to date. For example fibrinogen is a specific ligand for the platelet receptor (GPIIb-IIIa); vitronectin, von Willebrand factor and fibrinogen are specific ligands for the vitronectin receptor (VnR); fibronectin is a specific ligand for the VLA-5 receptor; laminin is a specific ligand for the VLA-6 receptor; and collagen is a specific ligand receptor for the VLA-2 receptor. The previous recitation of specific ligands is not intended to be limiting, but rather identifies more well characterized specific ligands for particular integrins, i.e., to identify representative integrin-ligand pairs that participate in specific binding. Other ligands and integrins may be utilized in the compositions and methods described herein.

Preferably an integrin-activating antibody in an antibody composition of this invention is a monoclonal antibody, and thus the antibody composition is referred to as a monoclonal antibody composition. The phrase "monoclonal antibody composition" in its various grammatical forms refers to a population of antibody molecules that contain only one species of antibody combining site capable of immunoreacting with a particular antigen. A monoclonal antibody composition thus typically displays a single binding affinity for any antigen with which it immunoreacts. A monoclonal antibody composition may therefore contain an antibody molecule having a plurality of antibody combining sites, each immunospecific for a different antigen, e.g., a bispecific monoclonal antibody.

An antibody or monoclonal antibody composition of the present invention is characterized as containing antibody molecules that immunoreact with an integrin and thereby increases the binding affinity of the integrin for binding to ligand. An antibody of this invention is referred to as an integrin-activating antibody to indicate the unique integrin-activating property of the antibody as described herein. An integrin-activating antibody is also characterized as immunoreacting with a ligand-induced binding site (LIBS) that is formed on an integrin-ligand complex when the integrin is specifically bound to a specific (predetermined) ligand.

Binding affinity between an integrin and a ligand to which it specifically binds can readily be measured using a variety of molecular binding approaches well known in the art, including equilibrium binding studies together with saturation point measurements and Scatchard plots, as described in Example 10. Increases in affinity of ligand binding can, therefore, be readily detected by comparing affinity of ligand binding under experimental conditions where the activating antibody is present or absent.

An antibody is considered an integrin-activating antibody if it induces, upon specific immunoreaction with the integrin, an increase of measured affinity of binding between the integrin and a specific ligand, i.e., an increase in ligand-binding affinity. Preferably the increase in affinity is greater than one order of magnitude, and more preferably greater than two orders of magnitude, in the measured dissociation constant (Kd) used to express binding affinity. Particularly preferred are integrin-activating antibodies that produce an affinity of specific ligand binding upon immunoreaction with the integrin that when expressed as a dissociation constant is greater than $10^{-5}$ M, and preferably is greater that $10^{-6}$ M. Exemplary is the affinity of Kd=110 nM for $\alpha_{IIb}\beta_3$ present on A5 cells when measured for binding fibrinogen in Example 10 after activation by the monoclonal antibody Ab-62.

An alternate assay for measuring integrin-activating activity detects immunoreaction of an activation-specific antibody with the integrin before and after activation. Activation-specific antibodies have been described for the integrin GPIIb-IIIa and are exemplary of the alternate assay as described in Example 10. Where an activation-specific antibody is available, the alternate assay is preferred because of the relative ease in measuring binding of an activation-specific antibody when compared to equilibrium binding studies to detect changes in dissociation constants.

In an activation-specific antibody binding assay, an integrin-activating antibody is typically measured by flow cytometry involving fluorescence activated cell sorting (FACS), such as described in Example 10. An antibody is considered integrin-activating if there is an increase, upon immunoreaction of integrin with the activating antibody, in the mean cell fluorescence intensity (MCFI) of the activated cells over the background (non-activated) cell population, in an amount of at least a three-fold increase in MCFI, and preferably about a ten-fold increase in MCFI.

An antibody is considered to immunoreact with a LIBS if the antibody preferentially binds ligand-occupied integrin when compared to immunoreaction with the non-bound (unoccupied) integrin. Preferential binding reflects a relative binding affinity and can be measured as described above by comparing antibody binding to (immunoreaction with) integrin in the presence or absence of ligand specific for that integrin. Comparative immunoreaction binding affinities are also conveniently measured experimentally as described in Example 2, and are therefore exemplary of a preferred means to identify an anti-LIBS antibody.

An antibody is designated as preferentially binding to a LIBS on a ligand-occupied integrin where there is detectable difference in antibody affinity for immunoreaction with integrin when present as an integrin-ligand complex as compared to unoccupied integrin such that the greater affinity is for the complex. Preferably, the difference in affinity is at least greater than about 20% when measured as described in Example 2 using the ratio (B/B$_0$) of immunoreaction product detectable in the presence (B) over absence (B$_0$) of competing integrin in a competition assay to determine an increase in the ratio when integrin specific ligand is added to the competition assay admixture and induces expression of the LIBS on the integrin.

In a preferred embodiment, an integrin-activating antibody has the additional property of immunoreacting with a LIBS epitope on an integrin with enhanced affinity. Enhanced affinity is measured using the same competition ELISA described in Example 2 as for identifying a LIBS on an integrin, as exemplified by the panel of antibodies characterized in Table 1.

An integrin-activating antibody has enhanced affinity for immunoreaction if the percentage change in $B/B_0$ upon addition of specific ligand to the competition ELISA immunoreaction admixture is greater than 25 percent, preferably greater than 30 percent and more preferably greater than 40% percent. The integrin-activating antibodies LIBSB, LIBSC, and LIBSF are particularly preferred members of the class of enhanced affinity integrin-activating antibodies. The property of enhanced affinity for these antibodies can be seen in Table 1, and provides the advantage of greater immunospecificity in the diagnostic and therapeutic methods described herein.

C. Methods for Producing Monoclonal Antibody Compositions

A monoclonal antibody composition is typically composed of antibodies produced by clones of a single cell called a hybridoma that secretes (produces) but one kind of antibody molecule. Historically, the hybridoma cell was formed by fusing an antibody-producing cell and a myeloma or other self-perpetuating cell line. Such antibodies were first described by Kohler and Milstein, *Nature* 256:495–497 (1975), which description is incorporated by reference although numerous variations have since been described for producing hybridoma cells, as is well known.

The preparation of monoclonal antibodies generally involves immunizing a mammal with an inoculum containing the integrin against which the antibody is to immunoreact, thereby inducing in the mammal antibody molecules having the immunospecificity described herein. The antibody-producing cells are then isolated, cloned and screened for the presence of antibody molecules of interest.

Thus the present invention contemplates a method of forming an integrin-activating monoclonal antibody that immunoreacts with an integrin and when immunoreacted increases the binding affinity of the integrin for binding to a preselected specific ligand, and that immunoreacts with a ligand-induced binding site expressed by an integrin-ligand complex where the complex contains the integrin specifically bound to a specific (preselected) ligand. The method comprises the steps of:

a) Immunizing an animal with an inoculum comprising an integrin. The integrin can be presented in a variety of forms, as described herein, although it is preferred that the integrin be present in the form of an integrin-ligand complex. Representative forms include purified integrin, purified integrin admixed with a specific ligand, such as described in Example 2, partially isolated integrin in the form of cell membranes having the cell surface integrin receptor associated with the membranes, such as is described in footnote e of Table 1 for antibody PM1-2, and whole cells having the integrin associated with the cell membrane, such as is described using intact platelets in Example 10 for antibody P41.

Where the integrin is $\alpha_{IIb}\beta_3$, it is preferred that the immunogen is a complex of GPIIb-IIIa and a GPIIb-IIIa specific ligand, such as fibrinogen, GRGDSP, the fibrinogen gamma chain, and the like. The immunization is typically accomplished by administering the inoculum to an immunologically competent mammal an immunologically effective amount, i.e., an amount sufficient to produce an immune response. Preferably, the mammal is a rodent such as a rabbit, rat or mouse. The mammal is then maintained for a time period sufficient for the mammal to produce cells secreting antibody molecules that immunoreact with the receptor-ligand complex.

The word "inoculum" in its various grammatical forms is used herein to describe a composition containing an integrin in one of the forms described above as an active ingredient used for the preparation of integrin-activating antibodies.

The inoculum contains an effective, immunogenic amount of an integrin, preferably in combination as an admixture with a specific ligand. The effective amount of integrin per unit dose sufficient to induce an immune response to the immunizing integrin depends, among other things, on the species of animal inoculated, the body weight of the animal and the chosen inoculation regimen as is well known in the art. Inocula typically contain protein concentrations of about 10 micrograms to about 500 milligrams per inoculation (dose), preferably about 50 micrograms to about 50 milligrams per dose.

The term "unit dose" as it pertains to the inocula refers to physically discrete units suitable as unitary dosages for animal, each unit containing a predetermined quantity of active material calculated to produce the desired immunogenic effect in association with the required diluent; i.e., carrier of vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the immunogen, for example an isolated integrin, by dispersing the immunogen in a physiologically tolerable (acceptable) diluent such as water, saline or phosphate-buffered saline to form an aqueous composition.

Inocula can also include an adjuvant as part of the diluent. Adjuvants such as complete Freund's adjuvant (CFA), incomplete Freund's adjuvant (IFA) and alum are material well known in the art, and are available commercially from several sources.

(b) A suspension of antibody-producing cells removed from the immunized mammal is then prepared. This is typically accomplished by removing the spleen of the mammal and mechanically separating the individual spleen cells in a physiologically tolerable medium using methods well known in the art.

(c) The suspended antibody-producing cells are treated with a transforming agent capable of producing a transformed ("immortalized") cell line. Transforming agents and their use to produce immortalized cell (transformed) lines are well known in the art and include DNA viruses such as Epstein Bar Virus (EBV), Simian Virus 40 (SV40), Polyoma Virus and the like, RNA viruses such as Moloney Murine Leukemia Virus (Mo-MuLV), Rous Sarcoma Virus and the like, myeloma cells such as P3X63-Ag8.653, Sp2/0-Ag14 and the like.

In preferred embodiments, treatment with the transforming agent results in the production of a hybridoma by means of fusing the suspended spleen cells with mouse myeloma cells from a suitable cell line by the use of a suitable fusion promoter. The preferred ratio is about 5 spleen cells per myeloma cell in a suspension containing about $10^8$ splenocytes. A preferred fusion promoter is polyethylene glycol having an average molecule weight from about 1000 to about 4000 (commercially available as PEG 1000, etc.); however, other fusion promoters known in the art maybe employed.

The cell line used should preferably be of the so-called "drug resistant" type, so that unfused myeloma cells will not survive in a selective medium, while hybrids will survive. The most common class is 8-azaguanine resistant cell lines, which lack the enzyme hypoxanthine-guanine phosphoribosyl transferase and hence will not be supported by HAT (hypoxanthine, aminopterin, and thymidine) medium. It is also generally preferred that the myeloma cell line used be of the so-called "non-secreting" type which does not itself produce any antibody. In certain cases, however, secreting myeloma lines may be preferred.

(d) The transformed cells are then cloned, preferably to monoclonality. The cloning is preferably performed in a tissue culture medium that will not sustain (support) non-transformed cells. When the transformed cells are hybridomas, this is typically performed by diluting and culturing in separate containers the mixture of unfused spleen cells, unfused myeloma cells, and fused cells (hybridomas) in a selective medium which will not sustain the unfused myeloma cells (non-transformed cells). The cells are cultured in this medium for a time sufficient to allow death of the unfused cells (about one week). The dilution can be a limiting dilution, in which the volume of diluent is statistically calculated to isolate a certain number of cells (e.g., 1-4) in each separate container (e.g., each well of a microtiter plate). The medium is one (e.g., HAT medium) that will not sustain the drug-resistant (e.g., 8-azaguanine resistant) unfused myeloma cell line.

(e) The tissue culture medium of the cloned transformants is then assayed (evaluated) to detect the presence of secreted antibody molecules having the immunoreactive properties as described herein using well known immunological screening techniques together with the assays described herein to identify integrin-activating antibodies.

As shown by the various screening protocols in Example 2 to identify integrin-activating antibodies, several separate assays are typically conducted to identify an antibody of this invention. First, the culture is evaluated for antibodies immunoreactive with the i-mmunogen. Cultures containing the integrin-immunoreactive antibodies are then further evaluated for the presence of antibodies that exhibit integrin-activating activity. Representative activation assays are described in Examples 2 and 10. Although not required, it is preferred to first screen for immunogen-reactive antibodies because the immunoreaction assay is more convenient than the activation assay and serves to limit the candidates for analysis of activating activity. However, nothing is to construe that the first screen is required; only that it is preferred.

(f) A desired transformant is then selected and grown in an appropriate tissue culture medium for a suitable length of time, followed by recovery (harvesting) of the desired antibody from the culture supernatant by well known techniques. The suitable medium and suitable length of culturing time are also well known or are readily determined.

Representative and preferred methods for producing integrin-activating monoclonal antibody compositions are described in Example 2.

Integrin-activating monoclonal antibodies that immunoreact with the integrin GPIIb-IIIa were identified in Example 2 and, when immunoreacted, are shown to activate the integrin. Similar integrin-activating antibodies can be isolated that activate other integrins using the procedures described therein, so long as the specific ligand is known and available for use in the screening step, and a source for using the integrin as an immunogen is available. Thus, the present invention provides methods applicable to generating antibodies that activate the vitronectin receptor, the laminin receptor VLA-6, fibronectin receptor VLA-5, collagen receptor VLA-2, and the like integrins.

To produce a much greater concentration of slightly less pure monoclonal antibody, the desired hybridoma can be transferred by injection into mice, preferably syngenic or semisyngenic mice. The hybridoma will cause formation of antibody-producing tumors after a suitable incubation time, which will result in a high concentration of the desired antibody (about 5-20 mg/ml) in the bloodstream and peritoneal exudate (ascites) of the host mouse.

A monoclonal antibody composition can be enriched in the desired antibody molecules by additional isolation methods such as immunoaffinity chromatography using solid phase affixed immunizing antigens, as described herein, or by using, for example, DEAE Sephadex to obtain the IgG fraction, if desired.

Media and animals useful for the preparation of these compositions are both well known in the art and commercially available and include synthetic culture media, inbred mice and the like. An exemplary synthetic medium is Dulbeccol's minimal essential medium [DMEM; Dulbecco et al., *Virol.* 8:396 (1959)]supplemented with 4.5 gm/l glucose, 20 mM glutamine, and 20% fetal calf serum. An exemplary inbred mouse strain is the Balb/c.

A monoclonal antibody composition can also be produced by methods well known to those skilled in the art of producing antibodies by recombinant DNA methods. Those methods include isolating, manipulating, and expressing the nucleic acid that codes for all or part of an immunoglobulin variable region including both the portion of the variable region comprised by the variable region of immunoglobulin light chain and the portion of the variable region comprised by the variable region of immunoglobulin heavy chain. Methods for isolating, manipulating, and expressing the variable region coding nucleic acid in procaryotic and eucaryotic hosts are disclosed in Robinson et al., PCT Publication No. WO 89/0099; Winter et al., European Patent Publication No. 0239400; Reading, U.S. Pat. No. 4,714,681; Cabilly et al., European Patent Publication No. 0125023; Sorge et al., *Mol. Cell Biol.*, 4:1730-1737 (1984); Beher et al., *Science*, 240:1041-1043 (1988); Skerra et al., *Science*, 240:1030-1041 (1988); and Orlandi et al., *Proc. Natl. Acad. Sci., U.S.A.*, 86: 3833-3837 (1989). Typically the nucleic acid codes for all or part of an immunoglobulin variable region that binds a preselected antigen (ligand). Sources of such nucleic acid are well known to one skilled in the art and, for example, may be obtained from a hybridoma producing a monoclonal antibody that binds the preselected antigen, or the preselected antigen may be used to screen an expression library coding for a plurality of immunoglobulin variable regions, thus isolating the nucleic acid.

See, for example, the method of isolating monoclonal antibodies from an immunological repertoire as described by Sastry et al., *Proc. Natl. Acad. Scr.*, 86:5728–5732 (1989); and Huse et al., *Science*, 246:1275–1281 (1989).

The monoclonal antibody compositions produced by the above method can be used, for example, in diagnostic and therapeutic modalities wherein activation of integrin is desired, as described further herein.

D. Hybridomas

Hybridomas of the present invention are those which are characterized as having the capacity to produce an integrin-activating monoclonal antibody composition of this invention.

A preferred hybridoma of the present invention is characterized as producing integrin-activating antibody molecules that immunoreact with an integrin and when immunoreacted activate the affinity of the integrin for its specific ligand. The antibody also immunoreacts with a LIBS, and preferably immunoreacts with a LIBS present on a beta subunit of the integrin, and more preferably immunoreacts with a LIBS on the GPIIIa subunit in a platelet-associated GPIIb-IIIa-fibrinogen complex.

Representative preferred hybridomas are prepared and described in Example 2. Particularly preferred are the hybridoma cultures designated LIBSb, LIBSc, LIBSf and PMI-2.

Hybridoma culture PMI-2 has been deposited pursuant to Budapest Treaty requirements with the American Type Culture Collection (ATCC), Rockville, Me. 20852, U.S.A., on Dec. 22, 1987, and was assigned accession number HB 9615.

This hybridoma was deposited in a depository affording permanence of the deposit and ready accessibility thereto by the public upon the grant of a patent, under conditions which assure that access to the hybridoma will be available during the pending of the patent application to those entitled to such access, and that all restrictions on the availability to the public of the hybridoma as deposited will be irrevocably removed upon the granting of the patent. The deposited hybridoma will be maintained by the ATCC, and all maintenance fees have been paid, for the term of the patent or 30 years from the date of deposit, whichever is longer, and in all events for at least five years after the date of the last request for access.

Methods for producing hybridomas producing (secreting) antibody -molecules having a desired immunospecificity, i.e., having the ability to immunoreact with a particular protein, an identifiable epitope on a particular protein and/or a polypeptide, are well known in the art and are described further herein. Particularly applicable is the hybridoma technology described by Niman et al., *Proc. Natl. Acad. Sci. USA*, 80:4949–4953 (1983), and by Galfre et al., *Meth. Enzymol.*, 73:3–46 (1981), which descriptions are incorporated herein by reference.

E. Therapeutic Methods and Compositions

Therapeutic methods and compositions are contemplated for activating integrins. These methods are useful to promote cell attachment mediated by the integrins and find application in a wide variety of cell types, tissues and system where attachment of cells is desired.

Thus in general the invention contemplates a method for activating an integrin that binds a specific ligand comprising contacting the integrin with a solution containing an activating amount of an integrin-activating antibody as described herein that is immunospecific for the integrin.

Typically the method is practiced on cells expressing the integrin on the surface of the cell, so the contacting occurs by admixing the cells in a solution with the integrin-activation antibodies to form an activation admixture. The admixture is preferably physiologically compatible with cell viability, preferably sterile, and more preferably compatible with admixture with blood to facilitate adding the admixture to the blood after or during integrin activation.

An activating amount of integrin-activation antibody is an amount sufficient to produce the desired result, namely to activate the integrin to a degree sufficient to promote the desired degree of adhesion of the cell expressing the integrin, and typically depends on the amount of integrin to be contacted for activation.

Insofar as integrin activation involves increasing the ligand binding affinity of an integrin, an activating amount of integrin-activating antibody is a ligand affinity increasing amount, and can be measured by correlating dosages administered to the increases in ligand affinity measured by the affinity binding methods described.

In preferred embodiments, whether the method is practiced in vitro or in vivo, an activating amount is an amount sufficient to provide at least one molar equivalent of integrin-activating antibody per molar equivalent of integrin to be activated. This amount is referred to as a stoichiometric amount of integrin-activating antibody. Although antibody affinity for immunoreaction is typically sufficient for an integrin-activating antibody to immunoreact stoichiometrically in dilute solutions, it is preferred that an activation amount is in the range of about 100 nanomolar (nM) to 1 millimolar (mM) preferably in the range of 1 to 100 micromolar (uM) and more preferably about 5 to 10 uM.

When an integrin-activating method is practiced in vitro, a liquid sample containing integrin, and preferably a physiological fluid containing cells that express cell surface integrin, are admixed with an activating amount of an integrin-activating antibody of this invention to form an activation admixture. The activating admixture is maintained under biological conditions compatible with the formation of an immunoreaction product and also compatible, if required, with cell viability for a time period sufficient for the integrin-activation antibody to immunoreact with the integrin and, when immunoreacted, activate the integrin.

When the integrin-activating method is practiced in vivo, an activating amount of an antibody composition containing a physiologically tolerable diluent and integrin-activating antibody molecules as described herein is intravenously administered to a mammal, and the mammal is maintained for a sufficient time period to allow the antibody molecules to immunoreact with any integrin present in the form of a LIBS-expressing receptor-ligand complex and form an activating immunoreaction product.

In preferred embodiments, a therapeutic composition for use in an integrin-activating method includes integrin-activating antibody molecules that immunoreact with the beta subunit of the heterodimer of the integrin. Particularly preferred are integrin-activating antibodies that immunoreact with the GPIIIa subunit of platelet glycoprotein GPIIb-IIIa. Exemplary compositions comprise one or more of the monoclonal antibodies secreted by the hybridomas LIBSb, LIBSc, LIBSf, PMI-2 or P41.

Particularly preferred are therapeutic compositions that include an integrin-activating antibody having enhanced affinity for immunoreaction with LIBS as described herein.

In one embodiment the invention contemplates a method for promoting adhesion of cells that express cell surface integrin. Adhesion of the cells to specific tissues and surfaces is promoted by activating the integrin and thereby increasing the specific ligand affinity of the integrin on the surface of the cell. This approach is particularly suited to applications where limiting cell mobility is desired because the end result is that the cell becomes more adherent to select targets after integrin activation.

For example, in cases of local vascular trauma, where blood vessel (vascular) surfaces in contact with the vascular fluid are damaged or ruptured, rapid platelet activation is desirable. In patients where platelet activation is otherwise delayed, or when accelerated targeting and depositing of platelets onto vascular surfaces is desired, activating the platelet integrin GPIIb-IIIa will promote platelet adhesion.

Thus a method for promoting adhesion of cells that express cell surface integrin to adhere to a vascular surface having vascular fluid in contact with the vascular surface, such as the inside surface of a blood vessel, comprises admixing an activating amount of an integrin-activating antibody of this invention with said vascular fluid having the cells to be adhered therein. Thereafter, the admixture is maintained for a period sufficient for the activating antibodies to immunoreact with the integrin and form activated integrin.

In one preferred embodiment, the method is useful to promote platelet depositing onto traumatized vasculature (ruptured or otherwise damaged blood vessels) where fibrinogen is exposed to the vascular fluid. Administration of activating amounts of anti-GPIIb-IIIa activating antibody directly to the circulation, or locally to the region of blood vessel damage, provides a means to in vivo admix the integrin-activating amount of the integrin-activating antibody with the integrin present on the platelets. Preferred dosages may vary, but typically include an amount sufficient to produce a blood concentration of about 1 to 100 uM, preferably about 5 to 10 uM of integrin-activating antibody. The maintenance step for immunoreaction between the admixed antibody and the target integrin occurs in vivo in this embodiment.

In a related embodiment, deposition of endothelial cells onto vascular surfaces such as the vascular fluid-exposed surface of a prosthesis, artificial organ, vascular shunt and the like synthetic surface in direct blood or plasma contact is desired to reduce unwanted thrombogenic responses to the synthetic surface. To target endothelial cells and promote their deposition onto the vascular fluid exposed surface of a prosthesis, an integrin-activating antibody is admixed according to the present methods with the endothelial cells to activate one of the several integrins typically found on the endothelial cell.

The choice of antibody immunospecificity in an integrin-activating antibody for use in a method to promote endothelial cell adhesion depends on the surface to which endothelial cell adhesion is desired, and the specific ligand present on the surface to which the activated endothelial cell integrin adheres.

For synthetic prosthetic materials which normally do not contain integrin-specific ligands on their vascular fluid exposed surfaces, it is convenient to coat or otherwise affix a specific ligand as a target for integrin binding onto the fluid exposed surface. Suitable specific ligands include collagen, fibronectin or laminin where the integrin to be activated is the VLA-2, VLA-5 or VLA-6 receptors, respectively. However, more preferred for promoting adhesion of endothelial cells due to the relative abundance of integrin on the endothelial cell is a vitronectin receptor specific lagand, namely vitronectin, fibrinogen or von Willebrand factor.

Thus in embodiments for promoting endothelial cell adhesion to vascular fluid exposed prosthetic surfaces, the method involves admixing an integrin-activating antibody immunospecific for an endothelial cell integrin with a vascular fluid containing the endothelial cells. Preferably the activating antibody is immunospecific for vitronectin receptor (VnR), more preferably immunospecific for the beta subunit of VnR, and still more preferably is an integrin-activating antibody having enhanced affinity for a LIBS on the beta subunit of VnR.

In practicing the method for promoting endothelial cell adhesion to vascular fluid exposed prosthetic surfaces, the endothelial cells can be admixed in vivo by intravenous administration of an integrin-activating antibody, or can be admixed ex vivo or in vitro such as by an extracorporeal shunt of vascular fluid containing endothelial cells or extraction of endothelial cells into an activating admixture as described herein. Activation of endothelial cells by the present methods using integrin-activating antibodies increases both the rate and extent of seeding of endothelial cells onto a prosthesis, by as much as 10 fold increases in both the number of cells adhering per unit surface of vascular fluid exposed surface and rate of cell adhesion.

Another embodiment contemplated for promoting cell adhesion according to the therapeutic methods of this invention involves directing endothelial cells to vascular fluid exposed surfaces such as traumatized blood vessel walls where wound healing is required, and tissues where other injuries, such as inflammation or infection mediated tissue damage would benefit by endothelial cell deposition. Damaged vessels and other injured tissues contain high levels of vascular fluid exposed collagen and are ideally suited to targeting collagen receptor-bearing endothelial cells by the integrin-activating methods described herein. In this embodiment, collagen receptor-activating antibodies immunospecific for collagen receptor are used to activate endothelial cells bearing collagen receptor integrin, such as VLA-2, according to the cell adhesion promoting method described herein.

In another embodiment for promoting and targeting cell adhesion, the invention provides a means to inhibit tumor cell mobility by increasing adherence and thereby reducing the likelihood of free circulation of disattached tumor cells, in turn restricting tumor infestation at sites distinct from the source of the tumor cell. In this embodiment, the general considerations described herein above apply, namely to select the immunospecificity of the integrin-activating antibody based on the class of integrin that predominates on the tumor cell, or based on the tissue to which tumor cell attachment is desired.

For example, for melanoma cells, which express vitronectin receptor on the cell surface, anti-vitronectin receptor activating antibodies are preferred for use in the methods described herein for promoting melanoma cell adhesion. Application of the tumor immobilization and/or targeting method described above is generally applicable to other tumor cell types and can be readily adapted by one skilled in the art of tumor biology.

The invention also contemplates the use of delivery devices for providing the therapeutic compositions of this invention to specific sites where activation of integrin-bearing cells and subsequent promotion of cell adhesion is desired.

For example, a dressing for wound healing is contemplated that is designed to deliver integrin-activating antibodies to the site of tissue trauma so that any cells expressing integrin on their surfaces can be induced locally to adhere to specific ligands in the vicinity of the wound. Thus a dressing comprises a support matrix containing a means for holding and releasing a therapeutic composition of this invention, and the holding and releasing means contains a therapeutically effective amount of the therapeutic composition in a pharmaceutically acceptable carrier.

A support matrix for use in a dressing can be any of a variety of materials including a typical sterile gauze, continuous film web or fibrous web, hydrogel polymers comprised of linear or cross linked hydroxyethyl acrylate or methacrylate, linear or cross linked partially neutralized acrylic acid, and copolymers thereof, acrylamide or acrylate esters and the like as are well known in the hydrocolloid arts.

The means for holding and releasing a therapeutic composition can be any of a variety of structures or compositions adapted to hold and release a therapeutic composition of this invention onto the support matrix of the dressing. Such means are well developed in the drug delivery arts and can be adapted for slow or quick release of the active ingredient as desired by adjusting factors such as porosity or stability of the holding structure, coatings and the like. Furthermore, the means can involve binders, slow or fast release compositions such as liposomal vesicles and other hydrated mediums included gels, films and the like.

Preferred therapeutic compositions for use in a dressing are those containing integrin-activating antibodies that immunoreact with the platelet integrin GPIIb-IIIa or the endothelial cell integrins described herein.

A therapeutically effective amount of a therapeutic composition of this invention in the context of a wound dressing depends on the application for which it is adapted, but typically is an amount designed to deliver about 5 nanomoles to 1 micromole of antibody per square centimeter of skin, tissue or surface onto which the dressing is applied.

As used herein, the terms "pharmaceutically acceptable," "physiologically tolerable" and its grammatical variations, as they refer to compositions,, carriers, diluents and reagents, are used interchangeably and represent that the materials are capable of administration to or upon a mammal without the production of untoward physiological effects such as nausea, dizziness, gastric upset and the like.

Preferably, for both the in vitro and in vivo methods, the antibody molecules are present as a monoclonal antibody composition and more preferably are those produced by one of the hybridomas LIBSb, LIBSc, LIBSf or PMI-2.

The antibody molecule-containing compositions when formulated for therapeutic compositions are physiologically administrable compositions and can take the form of solutions or suspensions.

The term "physiologically administrable composition" as used herein refers to solutions, suspensions and mixtures that are capable of being readily provided into the body of a mammal by parenteral, oral or rectal administration and includes injectable solutions, emulsions and the like. The preparation of a therapeutic composition that contains antibody molecules as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient as are well known. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents and the like which enhance the effectiveness of the active ingredient.

An integrin-activating antibody molecule composition can be formulated into a therapeutic composition in a neutralized pharmaceutically acceptable salt form. Pharmaceutically acceptable salts include the acid addition salts (formed with the free amino groups of the antibody molecule) that are formed with inorganic acids such as, for example, hydrochloric or phosphoric acids, or such organic acids as acetic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic antibody molecule-containing compositions are conventionally administered intravenously, as by injection of a unit dose, for example. The term "unit dose" when used in reference to a therapeutic composition of the present invention refers to physically discrete units suitable as unitary dosages for humans, each unit containing a predetermined quantity of active material calculated to produce the desired therapeutic effect in association with the required diluent, i.e., carrier, or vehicle.

The compositions are administered in a manner compatible with the dosage formulation, and in a therapeutically effective amount. The quantity to be administered depends on the subject to be treated, and capacity of the subject to utilize the active ingredient. Precise amounts of active ingredient required to be administered depend on the judgment of the practitioner and are peculiar to each individual. However, suitable dosage ranges are of the order of one to several milligrams of active ingredient per individual per day and depend on the route of administration. Suitable regimens for initial administration and booster shots are also variable, but are typified by an initial administration followed by repeated doses at one or more hour intervals, by a subsequent injection or other administration. Alternatively, continuous intravenous infusion sufficient to maintain therapeutically effective concentrations in the blood are contemplated. Therapeutically effective blood concentrations of antibody molecules of the present invention are preferably in the range of about 1.0 uM to about 100 uM, and more preferably about 5 to 10 uM.

F. Diagnostic Systems

A diagnostic system in kit form of the present invention includes, in an amount sufficient for at least one assay, a composition containing monoclonal antibody molecules or fragments thereof of the present invention, as a separately packaged reagent, together with a label that indicates the presence of an immunoreaction product. Instructions for use of the packaged reagent are also typically included.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In one embodiment, a diagnostic system is contemplated for determining the presence, and preferably the amount, of activation competence in an integrin and preferably in an integrin when present on the surface of a cell present in a vascular fluid sample, such as blood or plasma. The diagnostic system comprises a package containing integrin-activating antibody molecules that immunoreact with an integrin present on said cells. Preferably, the integrin-activating antibody molecules immunoreact with the beta subunit of an integrin. In a preferred embodiment for determining activation competence of platelets, the integrin-activating antibody molecules immunoreact with the GPIIIa subunit of the platelet protein GPIIb-IIIa.

A diagnostic system of the present invention preferably includes a label or indicating means capable of signaling the formation of a specifically bound complex containing an antibody molecule of the present invention.

As used herein, the terms "label" and "indicating means" in their various grammatical forms refer to single atoms and molecules that are either directly or indirectly involved in the production of a detectable signal to indicate the presence of a complex. "In Vivo" labels or indicating means are those useful within the body of a human subject and include $^{111}$In, $^{99}$Tc, $^{67}$Ga, $^{186}$Re, and $^{132}$I. Any label or indicating means can be linked to or incorporated in an antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel methods and/or systems.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas, et al.,, *Scand. J. Immunol.*, Vol. 8, Suppl. 7:7 23 (1978), Rodwell et al., *Biotech.*, 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention but is not itself an antibody molecule of the present invention. Exemplary specific binding agents are antibody molecules, complement proteins or fragments thereof, protein A and the like. Preferably, the specific binding agent can bind the antibody molecule of this invention when it is present as part of an activated-integrin complex.

In preferred embodiments the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect, for example, the presence or quantity of integrin-activation competent cells in a body fluid sample such as serum, plasma or urine. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. No. 3,654,090; No. 3,850,752; and No. 4,016,043, which are all incorporated herein by reference.

Thus, in preferred embodiments, antibody or antigen reagent component can be affixed to a solid matrix to form a solid support that is separately packaged in the subject diagnostic systems.

The reagent is typically affixed to the solid matrix by adsorption from an aqueous medium, although other modes of affixation, well known to those skilled in the art, can be used.

Useful solid matrices are well known in the art. Such materials include the cross-linked dextran available under the trademark SEPHADEX from Pharmacia Fine Chemicals (Piscataway, N.J.); agarose; polystyrene beads about 1 micron to about 5 millimeters in diameter available from Abbott Laboratories of North Chicago, IL; polyvinyl chloride, polystyrene, cross-linked linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packages discussed herein in relation to diagnostic systems are those customarily utilized in diagnostic systems. Such packages include glass and plastic (e.g., polyethylene, polypropylene and polycarbonate) bottles, vials, plastic and plastic-foil laminated envelopes and the like.

F. Assay Methods

The present invention contemplates any method that results in determining activation competence in cells having cell surface integrin. Preferably the method allows determination of the presence, and if desired, the degree of competence so that activation competence of a whole cell provides meaningful comparative data to related control cells. Degree of competence is measured by determining the amount of activated integrin on the cell to be assayed by the diagnostic methods.

Cells that express surface integrins participate in a variety of cellular processes depending on the ability of the cell surface integrin to become activated, i.e., to exhibit increased ligand binding affinity. The present methods are useful to detect deficiencies in activation competence by directly measuring the integrin protein's ability to become activated.

The methods for determining activation competence of cells having cell surface integrin generally involve admixing a sample of cells in a physiological fluid with an activating amount of integrin-activating antibodies of this invention to form an activation admixture. Thereafter the activating admixture is maintained under biological assay conditions and for a time period sufficient for said cell surface integrin to immunoreact with the admixed antibodies and form an activated integrin immunocomplex on the surface of the cells. The presence, and preferably amount, of the activated integrin immunocomplex formed is then determined to indicate the presence, and preferably degree of activation competence in the cell.

A variety of methods to detect activated integrin immunocomplex can be employed to determine the formed product, if any. Exemplary are the methods described in Example 10 involving binding an activation-specific ligand. An activation-specific ligand can be a labeled ligand that normally binds the integrin when activated but does not substantially bind nonactivated (resting) ligand. Exemplary is $^{125}$I-fibrinogen used in Example 10 to measure activation of platelets. Alternatively, an activation-specific ligand can be an antibody molecule that immunoreacts with the integrin when activated but does not substantially immunoreact with the integrin when present in resting state.

In the above diagnostic assay, a preferred method for assaying for the presence of the activated integrin immunocomplex comprises the steps of admixing the activated integrin immunocomplex with an activation-specific ligand to form a binding admixture, maintaining the binding admixture for a predetermined time period sufficient to bind to the immunocomplex and form a binding reaction product, and detecting the binding product formed and thereby the presence of activated integrin immunocomplex.

In preferred embodiments, the cells to be assayed are platelets, and the integrin-activating antibody immunoreacts with platelet protein GPIIb-IIIa. A particularly preferred method measures platelet activation competence using an anti-beta subunit integrin-activation antibody immunoreactive with the GPIIIa subunit as described in Example 10.

Those skilled in the art will understand that there are numerous well known clinical diagnostic chemistry procedures that can be utilized to form detectable immunocomplexes. Thus, while exemplary assay methods are described herein, the invention is not so limited.

Biological assay conditions are those that maintain the biological activity of the antibody molecules of this invention and the cells expressing integrin on their surfaces that are sought to be assayed. Those conditions include a temperature range of about 4 degrees C. (4C.) to about 45 C., preferably about 37 C., at a pH value range of about 5 to about 9, preferably about 7, and an ionic strength varying from that of distilled water to that of about one molar sodium chloride, preferably about that of physiological saline. Methods for optimizing such conditions are well known in the art.

EXAMPLES

The following examples are given for illustrative purposes only and do not in any way limit the scope of the invention.

1. Isolation of GPIIb-IIIa

A. Platelet Isolation

Sixty milliliters (ml) of whole human blood was collected in 5 ml of ACD (0.065 M citric acid, 0.0"5 M sodium citrate, 2% dextrose) containing hirudin (Sigma Chemical Co., St. Louis, Mo.) at a final concentration of 0.06 units per milliliter (U/ml) and centrifuged for 15 minutes at 120 x g. The resulting supernatant, designated platelet rich plasma (PRP), was recovered, isolated and further centrifuged for 15 minutes at 1200 x g to form a pellet of isolated platelets. The supernatant formed is collected and used as platelet-poor plasma in other assays.

B. GPIIb-IIIa Isolation from Platelets

A platelet pellet prepared as in Example 1A, was resuspended in 5 ml TBS (0.15 M NaCl, 0.2 M Tris, pH 7.4, 0.5 mM CaCl$_2$, 0.01 mM leupeptin) and sonicated on ice for 10 minutes at a maximum setting using a Model W-375 sonicator (Heat Systems Ultrasonics, Plainview, N.Y.). The sonicated suspension was twice frozen and thawed using a dry ice-methanol ice bath and stored at minus 20 C. The frozen-thawed platelet sonicate was layered on top of 5 ml of a sucrose solution (40% v/v in TBS), and centrifuged at 4 C. for one hour at 38,000 rotations per minute (RPM) in a SW41 centrifuge rotor (Beckman Instruments, Fullerton, Calif.) to form a milky colored infranatant. The milky-infranatant was then recovered and centrifuged at 43,000 RPM in a SW50.1 centrifuge rotor (Beckman) at 4 C. for one hour. The resulting pellet was resuspended in typically 1-2 ml TBS to form a platelet membrane solution, the protein concentration of which was determined to be in the range of 10-25 mg/ml, using the Bio-Rad Protein Assay Kit (Bio-Rad, Richmond, Calif.) according to the manufacturer's instructions.

The platelet membrane solution was again centrifuged in a SW50.1 centrifuge rotor as above and the resulting pellet was resuspended in 2 ml of extraction buffer (0.03 M Tris, pH 7.4, 0.01 mM leupeptin, 200 mM n-octyl-beta-D-glucopyranoside; Calbiochem-Behring, La Jolla, Calif.). The platelet membrane extract thus formed was admixed thoroughly by vortexing and then maintained at room temperature for 30 minutes. The extract was thereafter centrifuged at 45,000 RPM in a SW50.1 centrifuge rotor for 1 hour at 4 C. and the platelet membrane extract supernatant thus formed was recovered.

The recovered supernatant was applied to a LKB Ultrogel Aca 34 gel filtration column (3×97 cm, LKB Instruments, Gaithersburg, Md.) that had been equilibrated with 1 liter of column buffer (0.03 M Tris, pH 7.4, 0.1 mM $CaCl_2$, 0.1% n-octyl-beta-D-glucopyranoside) and 5 ml fractions were collected from the resulting column effluent. The optical density at 280 nanometers of each fraction was determined and fractions around the several peaks were combined to form a pool for each peak. Samples from each pool were analyzed by electrophoresis in 6% polyacrylamide slab gels using the reducing buffers and procedures described by Laemmli, Nature (London), 227:680–685 (1970), and low molecular weight protein standards ranging in size from 14.4 kilodaltons (KDa) to 92.5 KDa (Bio-Rad, Richmond, Calif.). The pool containing predominantly two protein species having molecular weights corresponding to GPIIb and GPIIIa, i.e., 120 KDa and 100 KDa, respectively was recovered. The protein concentration of the isolated GPIIb-IIIa preparation thus prepared was typically determined using the Bio-Rad Protein Assay Kits to be in the range of 0.3 to 0.8 mg/ml.

C. Polypeptide Affinity Isolation of GPIIb-IIIa

Synthesis of peptide of the formula Gly-Arg-Gly-Asp-Ser-Pro-Lys was accomplished using the technique of Merrifield, *J. Am. Chem. Soc.*, 85:2149-54 (1963) or purchased from Peninsula Laboratories (Belmont, Calif.). All peptides were greater than 90% homogenous when analyzed by high performance liquid chromatography (HPLC) utilizing a $C_{18}$ bondapak column and a 0-60% linear gradient of acetonitrile in 0.1% trifluoroacetic acid. Affinity matrices containing the immobilized peptide Gly-Arg-Gly-Asp-Ser-Pro-Lys were prepared by coupling the peptide to cyanogen bromide-activated Sepharose 4B (Pharmacia P-L Biochemicals, Piscataway, N.J.) according to the manufacturer's instructions. The affinity matrix containing the immobilized peptide was packed into columns ($0.7 \times 15$ cm) and equilibrated with PBS at pH 7.5 containing 50 nM octylglucoside, 1 mM phenylmethanesulfonylfluoride (PMSF), 1 mM $CaCl_2$ and 1 mM $MgCl_2$ at 4 C. The platelet membrane extract supernatant prepared according to Example 1B was applied to the affinity matrix containing Gly-Arg-Gly-Asp-Ser-Pro-Lys. The unbound proteins were eluted with 100 ml of PBS at pH 7.5, containing 25 mM octylglucoside, 1 mM PMSF, 1 mM $CaCl_2$, and 1 mM $MgCl_2$ (column buffer). Bound GPIIb-IIIa was then eluted by washing the column with 10 ml of column buffer containing the designated peptide at a concentration of 1.7 mM followed by another 10 ml of column buffer. Fractions of 2.5 ml each were collected, and the proteins in each fraction were analyzed by electrophoresis on sodium dodecyl sulfate-polyacrylamide gels (7.5%) after reduction with 10% 2-mercaptoethanol. The protein bands were visualized by staining with Coomassie Blue according to the methods described in *Current Protocols in Molecular Biology*, Ausubel et al., eds., John Wiley and Sons, N.Y., 1987.

D. Immunoaffinity Isolation of GPIIb-IIIa

An immunoaffinity column was prepared by coupling the antibody PMI-1 (which binds to GPIIb, ATCC, Rockville, Md.) to Affi-Gel 10 (Biorad, Richmond, Calif.) at 4 mg of antibody per ml of resin using the instructions provided by the manufacturer of the activated resin. Platelets prepared according to Example 1A ($6 \times 10^{10}$) were lysed in 1 ml of 50 mM octylglucoside in a column buffer consisting of 10 mM N-[2-hydroxyethyl] piperazine-N-[2'ethanesulfonic acid] (HEPES), 1 mM $CaCl_2$, 0.15 M NaCl, 1 mg/ml phenylmethane sulfonylfluoride (PMSF), 1.25 mg/ml N-ethyl-maleimide and 0.1 mg/ml leupeptin. The insoluble material was removed by centrifugation at 45,000 RPM in an SW 50.1 rotor for one hour at 4 C. The supernatant, designated as platelet lysate, was collected, the peptide Gly-Arg-Gly-Asp-Ser-Pro (GRGDSP) was admixed at 1 mM, and thereafter admixed with 2 ml of antibody-Affi-Gel 10 and maintained for 12 to 18 hours at 4 C. This admixture was then placed into a column and washed with 10 column volumes of column buffer containing 1 mM of the peptide Gly-Arg-Gly-Asp-Ser-Pro and 25 mM octylglucoside, and eluted with five column volumes of column buffer at pH 5 containing 25 mM octylglucoside and no peptide. The eluted fractions were immediately neutralized to pH 7.2, pooled and dialyzed against column buffer containing 5 mM octylglucoside. The protein concentration of the isolated GPIIb-IIIa preparation thus prepared was determined using the Bio-Rad Protein Assay Kit.

2. Preparation of Monoclonal Antibody Compositions

Monoclonal antibodies that activate GPIIb-IIIa and immunoreact with a ligand-induced binding site on GPIIb-IIIa were produced using standard hybridoma technology with exceptions as noted. Briefly, two Balb/c mice were each immunized intraperitoneally four times at one week intervals with increasing doses (1 ug, 10 ug, 25 ug, 50 ug and 100 ug, respectively) of immunogen consisting of the receptor-ligand complex comprised of affinity-isolated GPIIb-IIIa, as prepared in Example 1C (1.25 mg/ml) and peptide Gly-Arg-Gly-Asp-Ser-Pro at 3 mg/ml. The immunogen was diluted 1:1 in Complete Freund's Adjuvant for the first immunization, in Incomplete Freund's Adjuvant for the second and third immunization, and in normal saline for the fourth. Three days after the fourth immunization about $1 \times 10^8$ lymphocytes were isolated from the spleens of both mice, admixed into a suspension and fused with $5 \times 10^7$ P3X63AG8.053 mouse myeloma cells using 50% PEG 1500 as the cell fusion promoter. The resulting transformed (fused) antibody-producing cells (hybridomas) were initially transferred to 96-well microtiter plates at a density of about $1 \times 10^6$ cells per well and cultured in selective HAT media.

Tissue culture supernatants from about 2000 wells appearing to contain viable HAT resistant hybridoma cells after 8 days of culturing were screened in the ELISA assay described in Example 3A for the presence of antibody molecules that immunoreact with plastic-immobilized GPIIb-IIIa. About 44 hybridoma cultures were identified that produced GPIIb-IIIa-immunoreacting antibody molecules. The isolated hybridomas were then subcloned twice at limiting dilutions to provide about 1 cell per well. Twenty four of the resulting hybridoma cultures were shown to be of monoclonal origin on the basis of three criteria: (1) each supernatant was from a single cell focus and immunoreacted with GPIIb-IIIa in the ELISA screen, (2) each supernatant showed a single homogeneous band when analyzed by cellulose acetate gel electrophoresis according to the method described in *Monoclonal Antibodies: Principles and Practice*, J. W. Goding, ed., Academic Press, Inc., Orlando, Fla., 1983, and (3) each supernatant contained a single isotype of immunoglobulin when analyzed using the Mouse Ig Screening and Isotyping Kit according to the instructions provided by the manufacturer, Boehringer-Mannheim Biochemicals, Indianapolis, Ind. Results of the isotype analysis of some of the hybridoma supernatants characterized are shown in Table 1.

TABLE 1

GRGDSP Modulation Of LIBS Epitope Expression In ELISAs To Identify Anti-LIBS Monoclonal Antibody

| Mab | Subunit[a] Specificity | Isotype | B/B$_0$[b] − | + | % Decrease[c] |
|---|---|---|---|---|---|
| LIBSa | GPIIIa | G$_1$K | 0.61 | 0.32 | 48 |
| LIBSb | GPIIIa | G$_{2a}$K | 0.62 | 0.35 | 44 |
| LIBSc | GPIIIa | G$_1$K | 0.45 | 0.21 | 53 |
| LIBSd | GPIIIa | G$_{2b}$K | 0.79 | 0.62 | 22 |
| LIBSe | GPIIIa | G$_1$K | 0.82 | 0.52 | 37 |
| LIBSf | GPIIIa | ND[d] | 0.29 | 0.17 | 41 |
| LIBSg | GPIIIa | ND | 0.64 | 0.51 | 20 |
| LIBSh | GPIIIa | G$_{2a}$K | 0.38 | 0.28 | 26 |
| LIBSi | GPIIIa | G$_{2a}$K | 0.22 | 0.17 | 23 |
| PMI-2[e] | GPIIIa | G$_{2a}$K | 0.58 | 0.46 | 21 |
| Mab15 | GPIIIa | G$_1$K | 0.25 | 0.23 | 8 |
| Mab19 | GPIIIa | MK | 0.32 | 0.32 | 0 |
| Mab23 | GPIIIa | G$_{2a}$K | 0.17 | 0.15 | 12 |
| LIBSj | hGPIIb | MK | 0.90 | 0.70 | 22 |
| PMI-1[e] | hGPIIb | G$_{2b}$K | 0.98 | 0.36 | 63 |
| Mab13 | hGPIIb | G1K | 0.61 | 0.51 | 16 |
| Mab10 | hGPIIb | G$_1$K | 0.84 | 0.79 | 6 |
| Mab18 | lGPIIb | MK | 0.40 | 0.34 | 15 |
| Mab16 | lGPIIb | MK | 0.54 | 0.47 | 13 |
| Mab5 | lGPIIb | MK | 0.66 | 0.64 | 3 |
| LIBSk | | G$_1$K | 0.80 | 0.59 | 26 |
| Mab38 | | G$_1$K | 0.82 | 0.69 | 16 |
| Mab51 | | ND | 0.76 | 0.73 | 4 |
| LIBSm | | MK | 0.39 | 0.54 | −38 |

[a]Subunit specificity was determined by Western blotting as described in Example 2.
[b]B/B$_0$ indicates the ratio of the measured absorbance at A490 in the presence (B) of platelet lysate (equivalent to 5 × 10$^8$ platelets/ml) to the measured absorbance at A490 in the absence (B$_0$) of lysate. The ratio B/B$_0$ was determined both in the presence (+) of GRGDSP (1 mM) and in the absence (−) of GRGDSP.
[c]A change in B/B$_0$ upon addition of GRGDSP indicates the presence of a LIBS. Antibodies were considered to be anti-LIBS if the percent change in B/B$_0$ was greater than 20%.
[d]ND = Not determined.
[e]PMI-1 and PMI-2 were generated in a separate immunization and fusion using platelet membranes as the immunogen as described by Shadle et al., J. Cell Biol., 99:2056-60 (1984), and were screened for anti-LIBS activity as described herein.

The above screening procedure resulted in the identification of 22 hybridomas that produce antibody molecules that immunoreact with plastic-immobilized GPIIb-IIIa.

To identify hybridomas that produce antibody molecules that immunoreact with a ligand-induced binding site (LIBS) on GPIIb-IIIa (i.e., a GPIIb-IIIa LIBS), a competition ELISA screen was conducted as described in Example 3B discussed hereinafter, in which the immunoreaction admixture was maintained in the presence and absence of a GPIIb-IIIa specific ligand to express a GPIIb-IIIa LIBS. Anti-GPIIb-IIIa LIBS antibody molecules are those that exhibit a greater affinity of immunoreaction with GPIIb-IIIa when measured in the presence of a GPIIb-IIIa specific ligand as compared to the measurement in the absence of specific ligand, such that the greater affinity represents a change in the ratio of the absorbance at 490 nm (B/B$_0$) of greater than 20% when measured in the presence (as compared to the absence) of GPIIb-IIIa specific ligand.

Twelve hybridomas were identified from the group of twenty two hybridomas in Table 1 that produce antibody molecules that immunoreact with GPIIb-IIIa LIBS, and the hybridomas are designated herein as LIBSa-LIBSm, as shown in Table 1.

In addition, it is seen that other anti-LIBS antibody molecules have been isolated by the disclosed methods, as shown in Table 1, that immunoreact with other LIBS epitopes present on the GPIIb or GPIIIa subunits of the platelet receptor.

To identify hybridomas that produce integrin-activating monoclonal antibodies that immunoreact with the integrin GPIIb-IIIa and activate the integrin so that the affinity for ligand is increased, an activation assay was used as to screen the Mabs in Table 1. Two permutations of the activation assay are described in Example 10 and involve measuring the capacity of a putative activating antibody to increase the ability of GPIIb-IIIa to bind either PAC1, an activation-specific antibody, or fibrinogen, respectively.

Activating monoclonal antibodies were initially identified using the PAC1 binding assay, and include LIBSb (also referred to as Ab62), LIBSC, LIBSF, and PMI-2. These antibodies were considered to have integrin-activating activity because they increased FITC-PAC1 binding to platelets and induced a shift in mean cell fluorescence intensity (MCFI) of greater than three-fold MCFI when expressed as arbitrary fluorescence intensity units.

All of the activating antibodies identified herein including P41 described in Example 10, have been shown to also possess anti-LIBS immunoreactivity.

Particularly preferred are the antibodies that exhibit enhanced affinity for immunoreaction with a LIBS epitope as detected in Table 1. These are antibodies that exhibit greater than 25 percent, preferably 30 percent, and more preferably 40 percent, change in-B/Bo upon addition of the specific ligand.

The locations of the particular GPIIb-IIIa LIBS detected by the monoclonal antibodies shown in Table 1 were mapped to subunit regions of the platelet receptor by western immunoblotting according to the general methods described by Towbin et al., Proc. Natl. Acad. Sci U.S.A, 76:4350-54, (1979). Briefly, GPIIb-IIIa isolated in Example 1B was subjected to electrophoresis on 7.5% SDS polyacrylamide gels (SDS-PAGE) under reducing conditions, transferred to a membrane and immunoreacted with supernatants of the hybridomas shown in Table 1. The immunoreaction products formed between the monoclonal antibodies provided in the hybridoma supernatants and the GPIIb-IIIa protein subunits on the membranes were detected using biotinylated second antibody and avidin-conjugated peroxidase according to manufacturer's instructions (Vectastain ABC Method, Vector Laboratories, Burlingame, Calif.).

The results of the Western immunoblot mapping showed that most of the hybridoma supernatants contained antibody molecules that immunoreacted with a protein having an apparent molecular weight on SDS-PAGE of 120 kilodaltons (KDa), 20 KDa or 100 KDa, corresponding to GPIIb heavy chain (hGPIIb), GPIIb light chain (lGPIIb) or GPIIIa, respectively. In a few cases, the antibody molecules did not react with any of the isolated GPIIb-IIIa subunits, leaving their subunit specificity uncharacterized. The determined subunit specificities are shown in Table 1.

Thus it is seen that the monoclonal antibody molecule produced by hybridoma LIBSA for example, which antibody molecule is also referred to herein as LIBSa, immunoreacts with the GPIIIa subunit of the GPIIb-IIIa platelet receptor. In addition the LIBSA antibody molecule immunoreacts with the LIBS1 epitope present on a receptor-ligand complex comprised of GPIIb-IIIa and a GPIIb-IIIa specific ligand.

Monoclonal antibody compositions comprised of isolated antibody molecules were also prepared by isolating the antibody molecules from the ascites fluid of a mouse containing one of the hybridoma cell lines shown in Table 1 using protein A-Sepharose typically obtained from Pharmacia Inc. (Piscataway, N.J.) and used according to manufacturer's instructions.

The protein concentration of isolated antibody molecule compositions as needed was determined using the Bio-Rad Protein Assay Kit (Bio-Rad, Richmond, Calif.) according to the manufacturer's instructions.

To prepare a monoclonal antibody composition containing $^{125}$I-labeled antibody molecules, 350 microliters (ul) of PBS (0.15 M NaCl, 0.01 M sodium phosphate, pH 7.09) containing 1 milligram per milliliter (mg/ml) of the above isolated antibody molecules were admixed with 40 micrograms (ug) of chloramine-T and 1 millicurie (mCi) of carrier-free Na$^{125}$I (Amersham, Arlington Heights, Ill.). The resulting admixture was maintained for 5 minutes at about 20 C and then admixed with 20 ul of a 2 mg/ml sodium metabisulfite solution (2 mg/ml) and 20 ul of a potassium iodide solution. Thereafter, 800 ul of PBS containing 1% BSA were admixed followed by further admixture of disopropylfluorophosphate to a final concentration of 10 mM. The resulting admixture was maintained for 60 minutes at 22 C and then dialyzed against PBS. The specific activity of the resulting $^{125}$I-labeled antibody molecules was about 4.5 microCurie (uci) per ug.

Compositions containing Fab fragments from the above isolated antibody molecules were prepared by digestion with papain (200:1 weight per weight of Ig to papain) for 6 hours at 37 C following the methods of Mage et al., *Methods in Enzymology*, 70:142-150 (1980). Undigested Ig and Fc fragments were removed by chromatography on protein A-Sepharose. The resulting Fab fragments-containing compositions were then ready for use, or were $^{125}$I-labeled, as needed, using the same procedures as described above for monoclonal antibody compositions.

3. ELISA Assays

A. ELISA To Screen Monoclonal Antibodies

Antibody molecules contained in hybridoma culture supernatants were examined for their ability to immunoreact with GPIIb-IIIa immobilized on plastic. Fifty microliters (ul) of coating solution (0.1 M NaHCO$_3$, pH 8. 0, 0. 1% NaN$_3$) containing 10 ug/ml of isolated GPIIb-IIIa prepared in Example 1B were admixed into the wells of flat-bottom 96-well microtiter plates (Immulon 2; Dynatech Laboratories, Chantilly, Va.). The plates were then maintained for 60 minutes at 37 C to permit the GPIIb-IIIa to adsorb onto the walls of the wells. The coating solution was removed by shaking, the wells were rinsed twice with washing buffer (10 mM Tris at pH 7.4, 0.05% (v/v) TWEEN-20, 0.15 M NaCl, and 200 mg/ml merthiolate), and 200 ul of blocking solution [5% bovine serum albumin (BSA;w/v) in coating solution] were admixed into each well (solid support) to block excess protein sites.

The wells were maintained for 60 minutes at about 37 C and then the blocking solution was removed. About 50 ul of hybridoma culture supernatant diluted 1:1 in dilution buffer consisting of 0.1% (w/v) BSA in washing buffer was added to each well to form an immunoreaction admixture. The resulting solid/liquid phase immunoreaction admixtures were maintained at room temperature for 60 minutes to permit formation of a first solid phase-bound immunoreaction product between the solid phase-bound GPIIb-IIIa-ligand complex and admixed antibodies. The solid and liquid phases were then separated, the wells were rinsed twice with washing buffer, and excess liquid was removed by shaking.

Fifty ul of a solution containing horseradish peroxidase labeled goat anti-mouse IgG (Tago Inc., Burlingame, Calif.), diluted 1:1000 in dilution buffer was admixed into each well to form a second solid/liquid phase immunoreaction admixture (labeling immunoreaction admixture). The wells were maintained for 60 minutes at room temperature to permit formation of a second immunoreaction product between the labeled antibody and any solid phase-bound antibody of the first immunoreaction product and then rinsed twice with washing buffer to isolate the solid phase-bound label-containing immunoreaction products. Excess liquid was then removed from the wells.

Fifty ul of freshly prepared chromogenic substrate solution containing 4.0 mg/ml 0-phenylenediamine and 0.012% (v/v) hydrogen peroxide in CP buffer (243 ml of 0.1 M citric acid and 250 ml of 0. 2 M dibasic sodium phosphate per liter H$_2$O, pH 5. 0) were then admixed into each well to form a color developing-reaction admixture. After maintaining the color developing-reaction admixture for 10 minutes at about 20 C, 50 ul of 2 N H$_2$SO$_4$ were admixed into each well to stop the developing-reaction, and the resulting solutions were assayed for absorbance at 490 nanometers (nm) light wavelength using a Model 310 ELISA plate reader (Bio-Tek Instruments, Winooski, Vt.) .

Antibody molecule compositions were considered to contain anti-GPIIb-IIIa immunoreactive antibody molecules if the measured absorbance at 490 nm (A490) was at least 6 times above background i.e., above about 0.3 optical density units when measured at A490.

B. Competition ELISA To Detect Anti-LIBS Antibodies

Antibody molecules contained in antibody compositions were examined for their ability to immunoreact with GPIIb-IIIa LIBS in a competition ELISA conducted similarly to the ELISA described in Example 3A with the following exceptions as noted.

Before an antibody composition was added to a GPIIb-IIIa coated microtiter wells, 20 ul of ELISA assay buffer consisting of 10 mM TRIS-HCL at pH 7.4, 0.15 M NaCl, 0.05% (v/v) TWEEN-20, 0.02% (w/v) sodium merthiolate, 5 mM CaCl$_2$, 5 mM MgCl2 and 0. 1% (w/v) BSA was added to each microtiter well. Then 10 ul of a solution containing platelet lysate at $2 \times 10^7$ platelets per ml, prepared as in Example 1D, was added to one set of wells and platelet lysate was omitted from a second set of wells. To both sets, with or without platelet lysate, was added 10 ul of a second solution that contained either 0 or 5 mM of the RGD-containing polypeptide ligand GRGDSP in ELISA assay buffer. Thereafter, 10 ul of an antibody composition at 0.3 $\mu$g/ml was added to both sets of wells at an antibody concentration diluted in ELISA assay buffer so as to be the limiting component in the ELISA immunoreaction admixture. Antibody concentrations are present as a limiting component when it has been diluted in ELISA assay buffer to produce an optical density at A490 of about 1.0 when measured using the ELISA assay of Example 3A with the exception that ELISA assay buffer is used in place of dilution buffer.

The results obtained in each immunoreaction admixture were rdeasured for the presence of a developed color reaction as before. Absorbance measured in wells that contained no platelet lysate is referred to as $B_0$, and the absorbance measured in wells that contained platelet lysate is referred to as B. A ratio of absorbance is calculated for $B/B_0$, and expressed as measured either in the presence (+) or absence (−) of RGD-containing ligand (GRGDSP). The expression of a LIBS cryptic antigenic determinant is determined by calculating the percentage decrease observed in $B/B_0$ when ligand is added to the GPIIb-IIIa contained in platelet lysate in the immunoreaction admixture. A decrease upon addition of ligand in $B/B_0$ that exceeds 20% indicates an antibody molecule that immunoreacts with a LIBS epitope. Table 1 shows the results of Competition ELISA for monoclonal antibody molecules prepared in Example 2 that immunoreact with GPIIb-IIIa.

4. Expression of the GPIIIA Cryptic Determinant by Fibrinogen-Bound Platelets Platelet rich plasma (PRP) was prepared as in Example 1A and divided into 2 aliquots. In one aliquot, the platelets were stimulated to express functional GPIIb-IIIa (fibrinogen receptors) by admixture of adenosine diphosphate (ADP) to a 10 uM final concentration to produce ADP-stimulated platelets. As a negative control, the second aliquot of PRP received no stimulus to produce non-stimulated platelets.

$^{125}$I-labeled LIBSA (anti-LIBS1) Fab fragments, prepared by usual techniques from the $^{125}$I-labeled antibodies described in Example 2, were then admixed to a 0.8 uM final concentration with several samples of each of the PRP aliquots in the presence of varying concentrations of fibrinogen. The immunoreaction admixtures thus formed were maintained at 37 C. for 30 minutes to permit formation of labeled immunoreaction products, i.e., fibrinogen-bound platelet/$^{125}$I-anti-LIBS1 complexes. The label-containing immunoreaction products were then separated from unbound $^{125}$I-anti-LIBS1 by centrifugation of the platelets through a sucrose cushion of 0.3 ml of 20% sucrose in a Beckman Microfuge B (Beckman Instruments, Inc., Fullerton, Calif.) to form a platelet pellet. The amount of $^{125}$I-anti LIBS1 associated with the pellet was then determined by gamma counting.

FIG. 1 illustrates the results of this study, and demonstrates that anti-LIBS1 antibody molecules immunoreact with stimulated, fibrinogen-bound, platelets but do not substantially immunoreact with non-stimulated platelets. It is believed that the $^{125}$I-anti-LIBS1 observed as "bound" in the non-stimulated PRP aliquot was due to non-specific binding ("sticking") and/or the presence of a naturally occurring background level of stimulated, fibrinogen-bound platelets or platelets stimulated and bound as a result of handling. The concentration of fibrinogen required for a half-maximal increase in anti-LIBS1 binding was about 0.7 uM, which is approximately the $K_d$ for fibrinogen binding to platelets. These results therefore indicate that binding of fibrinogen, an Arg-Gly-Asp (RGD) amino acid residue sequence-containing ligand, by the GPIIb-IIIa cytoadhesion results in expression of an otherwise cryptic antigenic determinant. Thus, anti-LIBS1 antibody molecules, and antibody molecules of similar immunospecificity, can be used to assay for the presence and amount of stimulated, fibrinogen-bound platelets in a vascular fluid sample.

5. Expression of GPIIb-IIIa Cryptic Antigenic Determinants By Ligand Binding

A. Assay for Antibody Binding to Platelets That Express Cryptic Antigenic Determinants by Admixture Washed platelets were isolated as described in Example 1A, and were resuspended in 2 ml of calcium-free Tyrode's buffer (0.13 M NaCl, 0.0026 M KCl 0.002M $MgCl_2 \cdot 6H_2O$, 5 mM Hepes, 0.012 M $NaHCO_3$, pH 7.2) which was first treated by admixture with Chelex 100 (200–400 mesh sodium form, Bio-Rad Laboratories, Richmond, Calif.), maintained to complex any divalent cations present in the Tyrode's buffer and filtered to remove the complexed divalent cations from the buffer. The platelet suspension was then applied to a Sepharose CL2B column (40 ml total bed volume, Pharmacia, Inc., Piscataway, N.J.) equilibrated with the same Tyrode's buffer. The platelets were recovered in the void volume of the column in 4 to 5 ml. The washed platelets were then resuspended to a concentration of $1 \times 10^8$ per ml in the same Tyrode's buffer. The above-prepared washed platelet containing solution was than divided into aliquots. Monoclonal antibody compositions containing various concentrations of $^{125}$I-labeled LIBSA (anti-LIBS1) antibody molecules in Tyrode's buffer prepared as described in Example 2, were admixed first with 1) polypeptide GRGESP (0.8 mM), 2) polypeptide GRGDSP (0.8 mM) or 3) polypeptide GRGDSP (0.8 mm) plus ADP (10 mM). The $^{125}$I-labeled antibody/peptide admixtures were then admixed with the platelet aliquots containing about $1 \times 10^8$ platelets/ml. The resulting immunoreaction admixtures were then maintained for 30 min at 37 C. to permit expression of the cryptic antigenic determinant and to allow the formation of $^{125}$I-labeled immunoreaction products, i.e., ligand-bound platelet/$^{125}$I-antibody complexes. The label containing immunoreaction products were then separated from non-bound $^{125}$I-labeled antibody by centrifugation of the platelet aliquot through a sucrose cushion as described in Example 4, and the platelet-associated radioactivity was determined as before.

Figure 2:
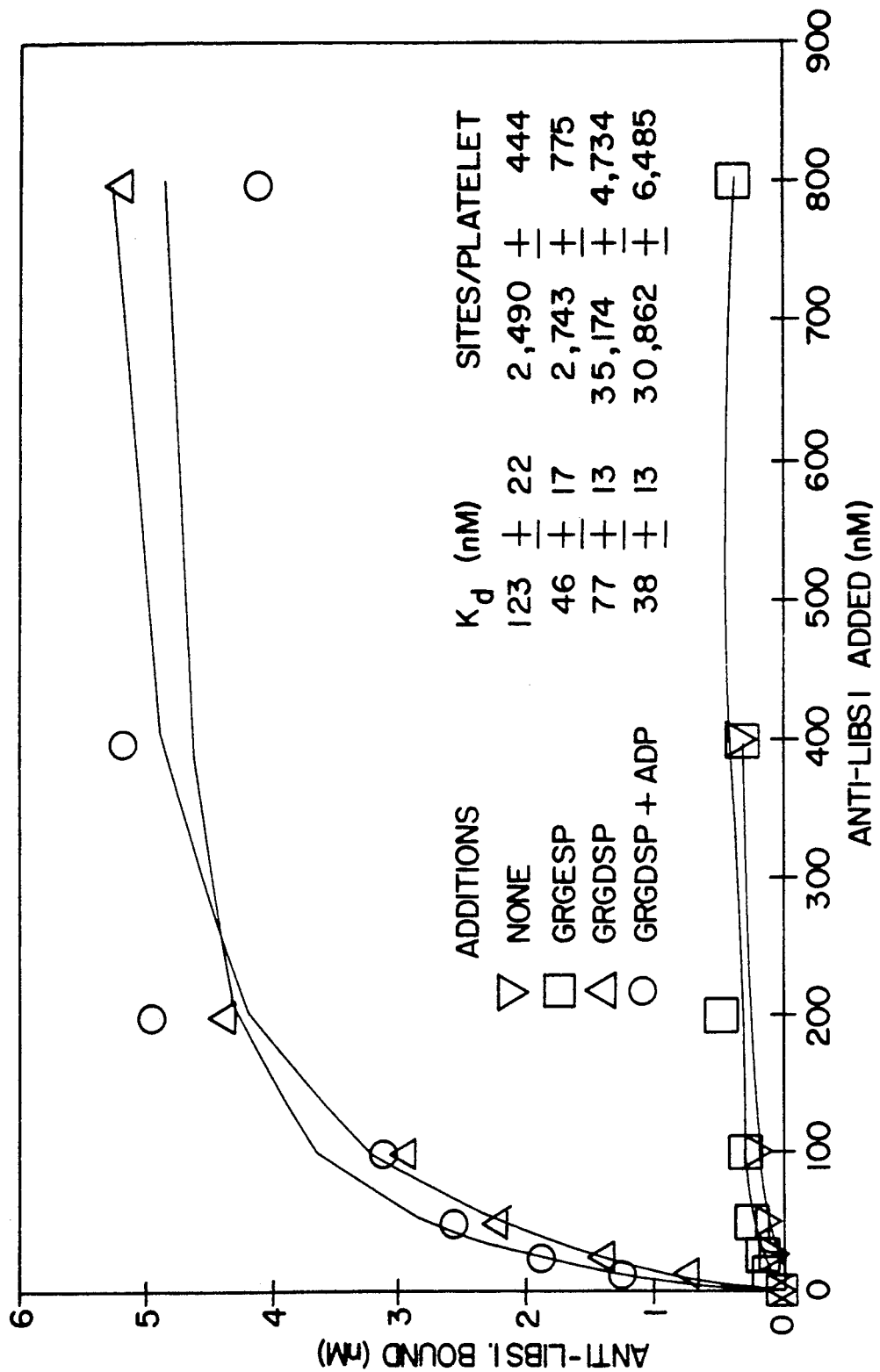
FIG. 2 illustrates anti-LIBS1 binding to platelets expressing a cryptic antigenic determinant as described in Example 5. Varied concentrations of $^{125}$I-anti-LIBS1 were bound at 37 C. for 30 minutes to gel-filtered platelets in the presence of no peptide (inverted triangle), 0.8 mM GRGESP (squares), 0.8 mM GRGDSP (triangles) or GRGDSP and 10 uM ADP (circles). Bound radioactivity was separated from free by spinning the platelets through a layer of sucrose.

The results are shown in FIG. 2, and are expressed as a plot of the amount of anti-LIBS1 added to the immunoreaction admixture versus the amount of platelet bound anti-LIBS1 detectable after immunoreaction. The results indicate that both stimulated and unstimulated platelets will express a LIBS1 cryptic antigenic determinant in the presence of the RGD-containing ligand GRGDSP. Further, the results indicated about $30-35 \times 10^3$ LIBS1 sites per platelet were detected using LIBS1 specific monoclonal antibody molecules.

Further, the results also indicate the structural specificity of the RGD-containing ligand for GPIIb-IIIa. A conservative substitution exchanging a glutamic acid (E) in place of the normally found aspartic acid residue (D) results in a peptide which is considerably less effective as a cryptic antigenic determinant inducing ligand.

B. Assay for Antibody Binding to Soluble Purified GPIIb-IIIa That Expresses Cryptic Antigenic Determinants.

The ability of various polypeptide ligands to induce the expression of a cryptic antigenic determinant was studied using soluble isolated GPIIb-IIIa.

To that end, the competition ELISA was performed as described in Example 3B with the following exceptions. Microtiter plates were coated using a coating solution containing isolated GPIIb-IIIa, prepared as described in Example 1B, at a concentration of 10 ug per ml. After blocking, all solutions used were Chelex 100-treated before use, as described for Tyrode's buffer in Example 5A.

Before an antibody composition was added to the GPIIb-IIIa coated microtiter well, 30 ul of a solution of dilution buffer containing (1) 2 mM $CaCl_2$; (2) immunoaffinity isolated GPIIb-IIIa or peptide affinity isolated GPIIb-IIIa, prepared as described in Example 1 and at a concentration of about 40 ug/ml; and (3) polypeptide GRGDSP, or GRGESP, at a final concentration of 1 mM, or no polypeptide, was added to each well. Thereafter, 10 ul of a solution of dilution buffer containing either LIBSA or Mab15 antibody molecules diluted to a limiting concentration as described in Example 3B was admixed into each well to form an immunoreaction admixture. Mab15 is a control antibody molecule that immunoreacts with GPIIb-IIIa but is not an anti-LIBS antibody. The immunoreaction admixtures were maintained at 22 C. for 16-20 hours to permit formation of a first solid phase-bound immunoreaction product between the solid phase-bound GPIIb-IIIa and the admixed antibodies. Thereafter, the amount of immunoreaction product formed was measured by forming a developed color reaction product and detecting the amount of colored product formed as before. Results of the measured immunoreaction is expressed as an apparent GPIIb-IIIa concentration (ug per ml) of the soluble GPIIb-IIIa in the immunoreaction admixture and is calculated as follows. The competition ELISA was first conducted using known GPIIb-IIIa concentrations in the absence of polypeptide to prepare a standard curve of immunoreaction results to obtain A490 measurements using a limiting amount of antibody molecule (i.e., a 1.0 O.D. amount). From the standard curve, any particular A490 measurement can be extrapolated to determine the apparent GPIIb-IIIa concentration present in the immunoreaction admixture. From the above A490 measurements, obtained in the presence of the indicated polypeptides, antibodies and GPIIb-IIIa preparations, apparent GPIIb-IIIa concentrations were calculated and are shown in Table 2.

TABLE 2

| LIBS1 Epitope Expression In Purified GPIIb-IIIa Is Increased By Ligand | | |
|---|---|---|
| | Apparent [GPIIb-IIIa] ug/ml | |
| | LIBSa | Mab 15 |
| Immunoaffinity Purified GPIIb-IIIa | | |
| No Peptide | 7.1 ± 0.8 | 52.2 ± 1.4 |
| GRGDSP (1 mM) | 35.7 ± 5.8 | 56.1 ± 0.2 |
| GRGESP (1 mM) | 12.9 ± 1.9 | 47.7 ± 1.4 |
| RGD-Affinity Purified GPIIb-IIIa | | |
| No Peptide | 23.9 ± 0.4 | 90.5 ± 2.7 |
| GRGDSP (1 mM) | 56.7 ± 1.0 | 95.5 ± 10.7 |
| GRGESP (1 mM) | 30.9 ± 3.2 | 101.7 ± 5.7 |

The results in Table 2 show that RGD-containing polypeptide ligands induce the expression of a cryptic antigenic determinant by GPIIb-IIIa in a manner analogous to that observed using intact platelets (see e.g., FIG. 2). The specificity of ligand-induced expression was verified by using a polypeptide having a conservative substitution (GRGESP), and was further verified by observing no significant ligand influence upon Mab15 monoclonal antibody binding. These results indicate that ligand-induced expression of the cryptic antigenic determinant (i.e., LIBS) recognized by an anti-LIBS1 monoclonal antibody (LIBSA) is an intrinsic property of GPIIb-IIIa, and not dependent upon GPIIb-IIIa association with platelets.

6. Preparation of Transfected Cell Lines Expressing Beta$_3$ (B$_3$) Integrins

To analyze the basis of affinity modulation of integrin function, cloned stable Chinese hamster ovary (CHO) cell lines expressing recombinant integrins of the $\beta_3$ family, namely $\alpha_{IIb}\beta_3$ (GPIIb-IIIa) and $\alpha_v\beta_3$ (vitronectin receptor), were prepared.

CHO cells were cotransfected with equal amounts of $\beta_3$ and $\alpha_{IIb}$ or $\alpha_v$ expression constructs [O'Toole et al., Blood, 74:14–18 (1989)], and a CDM8 vector containing the neomycin resistance gene (CDNeo) in a 30:1 ratio. Transfection was by the calcium phosphate [Graham et al, Virol., 52:456 (1973)] method followed by a 4 minute 15% glycerol shock. Forty eight hours after shock, cells were resuspended in selection media containing 700 ug/ml G418 and resistant colonies isolated after 2 weeks in culture. Positive clones were identified by flow cytometry described in Example 7 using subunit specific antibodies specific for the integrin subunits $\beta_3$, $\alpha_{IIb}$ and $\alpha_v$. Cloned cell lines were then established by single cell sorting in a FACStar (Becton-Dickinson, San Jose, Calif.) and maintained in media without G418. Cell lines A5 and VNRC3 were thereby isolated that exhibit bright and uniform staining with the antibodies Ab15 or Tab, and with Ab15 or LM142, respectively, and were maintained for further study.

7. Flow Cytometry to Characterize Human $\beta_3$ Integrins on Cell Surfaces

Antibody binding to cells was analyzed by flow cytometry, also referred to as fluorescence-activated cell sorting (FACS). Cells for flow cytometric analysis were harvested with 3.5 mM EDTA and an aliquot of $5 \times 10^5$ cells was pelleted, resuspended in media or Tyrodes buffer containing a specific first antibody, and incubated for 20 minutes on ice with or without peptide ligands. Cells were pelleted, washed once, and incubated for 20 minutes with the second antibody, FITC-conjugated goat anti-mouse IgG (Tago, Burlingame, Calif.). Cells were then pelleted, resuspended in 0.5 ml media or Tyrodes and analyzed on a FACS IV analyzer (Becton-Dickinson, San Jose, Calif.).

Monoclonal antibodies of known specificity were used in FACS analysis to identify integrin subunits on cell surfaces. Integrin $\alpha_{IIb}\beta_3$ complex-specific monoclonal antibodies (Mab) 4F10 and 2G12 were provided by Virgil Woods (University of California, San Diego, Calif.). $\alpha_{IIb}\beta_3$ complex-specific Mab 10E5 was provided by Barry Coller (State University of New York, Stony Brook, N.Y.). Mab specific for $\alpha_{IIb}$ designated Tab was provided by Roger McEver (University of Texas, San Antonio, Tex.). LM142, a Mab specific with the vitronectin receptor alpha subunit $\alpha_v$, was supplied by David Cheresh (Scripps clinic and Research Foundation, La Jolla, Calif.). PAC1, a GPIIb-IIIa activation specific Mab, was provided by Sanford Shattil (University of Pennsylvania, Pa.). Ab15 is a $\beta_3$ specific Mab prepared in the inventors' lab using purified GPIIb-IIIa as the immunogen.

Using FACS, the A5 and VNRC3 cell lines produced in Example 6 were characterized for the presence of human integrin subunits. The results of the FACS analysis are shown in Table 3.

TABLE 3

Reactivity of VNRC3 ($\alpha_v\beta_3$) and A5 ($\alpha_{IIb}\beta_3$) CHO Transfectants with Monoclonal Antibodies[a]

| Antibody (Specificity) | Cell Type | | |
|---|---|---|---|
| | A5 | VNRC3 | CHO |
| Tab ($\alpha_{IIb}$) | 265.3 | 5.2 | 4.5 |
| Ab15 ($\beta_3$) | 280.7 | 29.9 | 4.4 |
| 10E5 ($\alpha_{IIb}\beta_3$) | 269.5 | 4.1 | 4.9 |
| LM142 ($\alpha_v$) | 7.0 | 33.1 | 4.5 |
| None | 6.2 | 4.3 | 4.5 |

[a] Stable cloned CHO cell lines transfected with the $\beta_3$ and $\alpha_v$ or $\alpha_{IIb}$ subunits were stained with the indicated antibodies and analyzed by FACS. Results are expressed as mean florescence intensity in arbitrary units. The VNRC3 cell line expressed approximately 1/9 of the $\beta_3$ subunit that A5 does.

The results in Table 3 show that the cell lines expressed surface antigenic determinants appropriate for the transfected integrin subunits. The A5 line was strongly positive for $\alpha_{IIb}$ (Tab), $\alpha_{IIb}\beta_3$ (4F10), and $\beta_3$ (Ab15) but not for $\alpha_v\beta_3$ (LM142). For comparison the VNRC3 line which expresses $\alpha_v\beta_3$ was strongly positive with LM142, and Ab15, but negative with 4F10 and Tab. In addition, by using conventional immunoprecipitation of cell surface radio-iodinated A5 or VNRC3 cells according to Plow et al., Proc. Natl. Acad. Sci. USA, 83:6002-6006 (1986), $\alpha_{IIb}$ subunits from A5 cells and $\alpha_v$ U, from VNRC3 cells were immunoprecipitable with an anti-human $\beta_3$ antibody (Ab15) indicating that they were both complexed with the common transfected $\beta_3$ subunit. These data indicate that A5 cells express heterodimeric integrin comprised of the $\alpha_{IIb}$ and $\beta_3$ subunits, whereas VNRC3 cells express heterodimeric integrin comprised of the $\alpha_v$ and $\beta_3$ subunits.

8. Recombinant Integrins Bind Immobilized Fibrinogen

The capacity of A5 cells bearing recombinant $\alpha_{IIb}\beta_3$ to bind to immobilized fibrinogen (Fg) was evaluated by FACS analysis.

Immobilized Fg was prepared by coating 0.8 uM fluorescent latex beads (Fluoricon Fluorescent Particles, Baxter, McGraw Park, Ill.). These beads were prepared by incubating 1 mg of purified Fg with 650 ul of Fluoricon beads for 1 hour at room temperature. The beads were pelleted, resuspended in 1 ml of 30 mM Tris pH 7.4, 170 mM NaCl and 1% BSA, and stored at 4 degrees until ready for use. The binding of these particles to transfected cells was assessed by incubating $5 \times 10^5$ cells with 25 ul of beads in the presence or absence of polypeptide inhibitors for 30 minutes at room temperature. The solution was layered over a 6% BSA cushion, spun 5 minutes in a microfuge and the pelleted cells resuspended in 500 ul of Tyrodes and subjected to FACS analysis as described in Example 7.

The A5 cell line adhered to Fg-coated microspheres and adherence was inhibited with 2 mM GRGDSP peptide. In contrast, the parent CHO cell line failed to adhere. Thus, as in resting platelets [Coller, Blood, 55:169-178 (1980)], recombinant $\alpha_{IIb}\beta_3$ mediates cell binding to immobilized Fg.

9. Recombinant $\alpha_{IIb}\beta_3$ is Expressed as an Inactive Integrin

Platelet $\alpha_{IIb}\beta_3$ requires cellular activation to bind fluid phase macromolecular ligands, such as Fg, with high affinity [Coller, J. Cell Biol., 103:451-456 (1986); Shattil et al., J. Biol. Chem., 262:992-1000 (1987)]. To determine whether the recombinant $\alpha_{IIb}\beta_3$ was expressed on A5 cells in an activated form, the monoclonal anti $\alpha_{IIb}\beta_3$ antibody, PAC1, which is reactive with activated but not resting platelets [Shattil et al., J. Biol. Chem., 260:11107-11114 (1985)], was used in an FACS assay.

To that end, PAC1 antibody was fluoresceinated with FICT as described by Taub et al., J. Biol. Chem., 264:259-265 (1989) to form FITC-PAC1 and used directly in flow cytometry. Briefly, $5 \times 10^5$ cells were harvested and resuspended to 50 ul in Tyrodes buffer [Frelinger et al., J. Biol. Chem., 265:6346-6352 (1990)]containing 10 ug/ml of FITC-PAC1 in the presence or absence of additional agonists. After a 30 minute incubation at 37 degrees, the samples were diluted to 0.5 ml with Tyrodes and analyzed by flow cytometry as described in Example 7.

The activation specific monoclonal antibody PAC1 did not react with $\alpha_{IIb}\beta_3$ in the A5 cell line or with resting platelets although the receptor was present on both A5 cells and resting platelets as evidenced by staining with the $\alpha_{IIb}\beta_3$ complex specific antibody 4F10 using the FACS assay. In contrast, ADP activated platelets stained brightly with PACT by the FACS assay. Platelet agonists such as ADP (10 to 50 uM), thrombin (1 to 5 units/ml), epinephrine (4 to 200 uMO, phorbol myristate acetate (5 to 500 nm), and ionomycin (5 to 200 nM) failed to stimulate PACT binding to A5 cells. Three possible explanations for this result are: 1) the recombinant $\alpha_{IIb}\beta_3$ lacks the PACT epitope, 2) the recombinant $\alpha_{IIb}\beta_3$ cannot be activated, or 3) the CHO cells lack receptors and/or transduction systems required for agonist-mediated activation.

10. Activation of Integrin Using Activating Anti-Integrin Antibodies

To evaluate the capacity of a monoclonal antibody to activate (i.e., to increase specific ligand binding affinity of) the integrin GPIIb-IIIa, an assay was developed that measures PACT binding to GPIIb-IIIa bearing cells using the FACS analysis as described in Example 7.

In the PAC1-binding assay for integrin-activating antibody, the activating antibody was admixed with an integrin binding cell at a concentration of about 5 uM antibody. For GPIIb-III$_a$, a suspension of cells was prepared as in Example 9, activating antibody was admixed at 5 uM and the admixture was maintained for 20 minutes on ice. Thereafter FITC-PAC1 was added as described in Example 9 and the FACS protocol followed as in Example 9 to measure PAC1 binding.

Monoclonal antibodies (Mabs) were prepared essentially as described in Example 2 except using intact platelets as the immunogen. Ruggeri et al., S. Clin. Invest., 76:1950-58 (1985). Of 46 Mabs isolated that immunoreact with immunizing platelets, 6 were found that increased PACT binding to platelets when measured by the PAC1-binding assay and were designated as integrin-activating antibodies because the shift in mean cell fluorescence intensity (MCFI) was greater than a three-fold increase over background.

In the panel of Mabs isolated by immunization with intact platelets, P41 was selected from the 6 identified Mabs for further study.

Several anti-LIBS Mabs prepared in Example 2 and identified in Table 1 were also tested for integrin-activating activity as described above by measuring increased PAC1 binding in the PAC1-binding assay. By that assay, the anti-LIBS antibodies LIBSb, LIBSc and LIBSf described in Table 1 were identified that stimulate PAC1 binding.

Figure 3A:
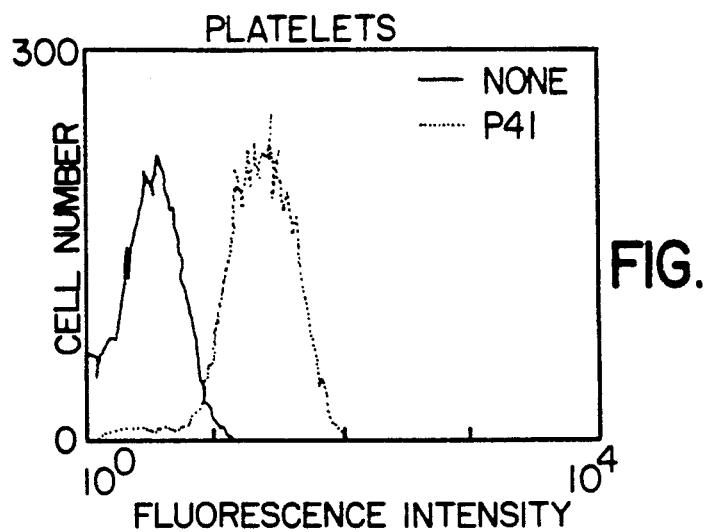
FIGS. 3A, 3B, and 3C illustrate the FACS analysis of the PAC1-binding assay described in Example 10 where the P41 Fab fragment was used to activat tegrin on platelets (FIG. 3A), A5 cells (FIG. 3B), and on CHO cells (FIG. 3C). For this assay, Fab fragments of the integrin-activating antibody, P41, were prepared and admixed with a separate suspensions of integrin binding cells at an antibody concentration of about 5 uM. The admixtures were maintained on ice for 20 minutes after which time FITC-PAC1 was added. The cells were then subjected to FACS analysis. The FACS profiles are presented with cell number plotted on the Y-axis and increasing fluorescent intensity plotted on the X-axis. Significant increases in PAC1-binding by treatment of cells with P41 Fab were indicated by a shift in mean cell fluorescence intensity (MCFI) greater than threefold over background. The P41 Fab fragment increased PAC1 binding to platelets and A5 cells but not to CHO cells.
Figure 3B:
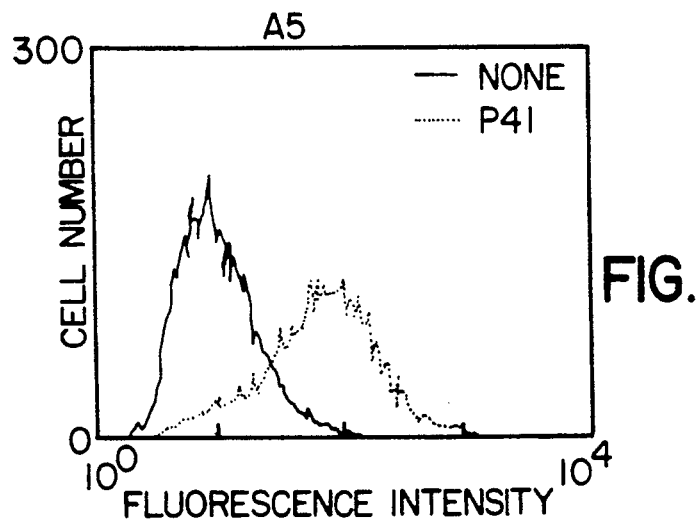
Figure 3C:
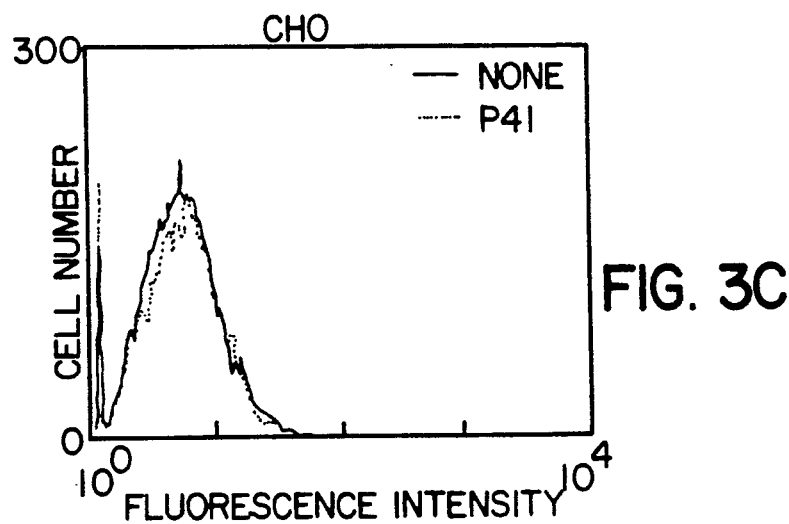

Fab fragments were prepared from the integrin-activating P41 or Ab62 antibodies using the Fab preparation procedure described in Example 2. Both the P41 Fab fragment or the Ab62 Fab fragment increased PAC1 binding to platelets, and to A5 cells, but not to CHO cells, when measured by the PAC1-binding assay. FIGS. 3A, 3B, and 3C show the FACS results of the PAC1-binding assay using the P41 Fab fragment to activate integrin on cells. Fab fragments of LIBSb also activated PAC1 binding to platelets or A5 cells in the PAC1-binding assay.

An independent measure of integrin activation was made by detecting the ability of a cell containing the integrin to bind soluble fibrinogen (Fg) that had been labelled with $^{125}$I. Fg was isolated and labelled with $^{125}$I by standard methods as described by Marguerie et al., *J. Biol. Chem.*, 255:154–161 (1980) to form $^{125}$I-Fg. Thereafter, the binding of $^{125}$I-Fg to transfected cells was assayed as described previously for platelets [Marguerie et al., *J. Biol. Chem.*, 255:154–161 (1980)]. Binding was initiated by the addition of cells to radiolabelled Fg and incubation at 37 degrees for 30 minutes. Bound ligand was separated from free ligand by centrifugation through 0.3 ml of 20% sucrose and the amount of radiolabelled ligand associated with the cell pellet determined by gamma detection.

When Fab fragments of the Mabs P41 or LIBSb (also referred to as Ab-62) were separately admixed at 5 uM with the A5 cells to activate the integrin prior to the $^{125}$I-Fg binding assay, each Fab was observed to stimulate a three fold increase in the number of $^{125}$-Fg molecules that bound the A5 cells. Unstimulated A5 cells or CHO cells exhibited no increase in binding to $^{125}$I-Fg above background. Background binding in this assay detected about 30,000 molecules of Fg bound per integrin bearing cell, whereas maximum Ab-62 stimulated A5 cells bound about 95,000 molecules of Fg per cell. In addition, soluble $^{125}$I-Fg binding was inhibited with the polypeptide GRGDSP, and was inhibited with the anti $\alpha_{IIb}\beta_3$ monoclonal antibody 2G12, but was not inhibited with the inactive polypeptide GRGESP.

The peptides RGDF, GRGDSP, GRGESP, and LGGAKQAGDV (L10) were prepared by solid phase synthesis on an Applied Biosystems model 430 peptide synthesizer (Foster City, Calif.) using phenylacetamidomethyl resins and t-butoxycarbonyl amino acids purchased from Applied Biosystems.

Equilibrium binding of soluble Fg to Ab-62 stimulated (activated) A5 cells was carried out to better characterize Fg binding. Time course analysis showed that Fg binding reached steady state by 30 minutes incubation and was >75% reversible. A5 cells ($10^6$ per ml) were incubated with 6 uM Sepharose-purified Ab-62 for 30 minutes at 22 C. to activate the integrin. Thereafter $^{125}$I-Fg was admixed in varying concentrations from 0.01 to 1 nM. After 60 minutes, bound Fg was measured as described above after centrifugation of the cells through sucrose.

Figure 4:
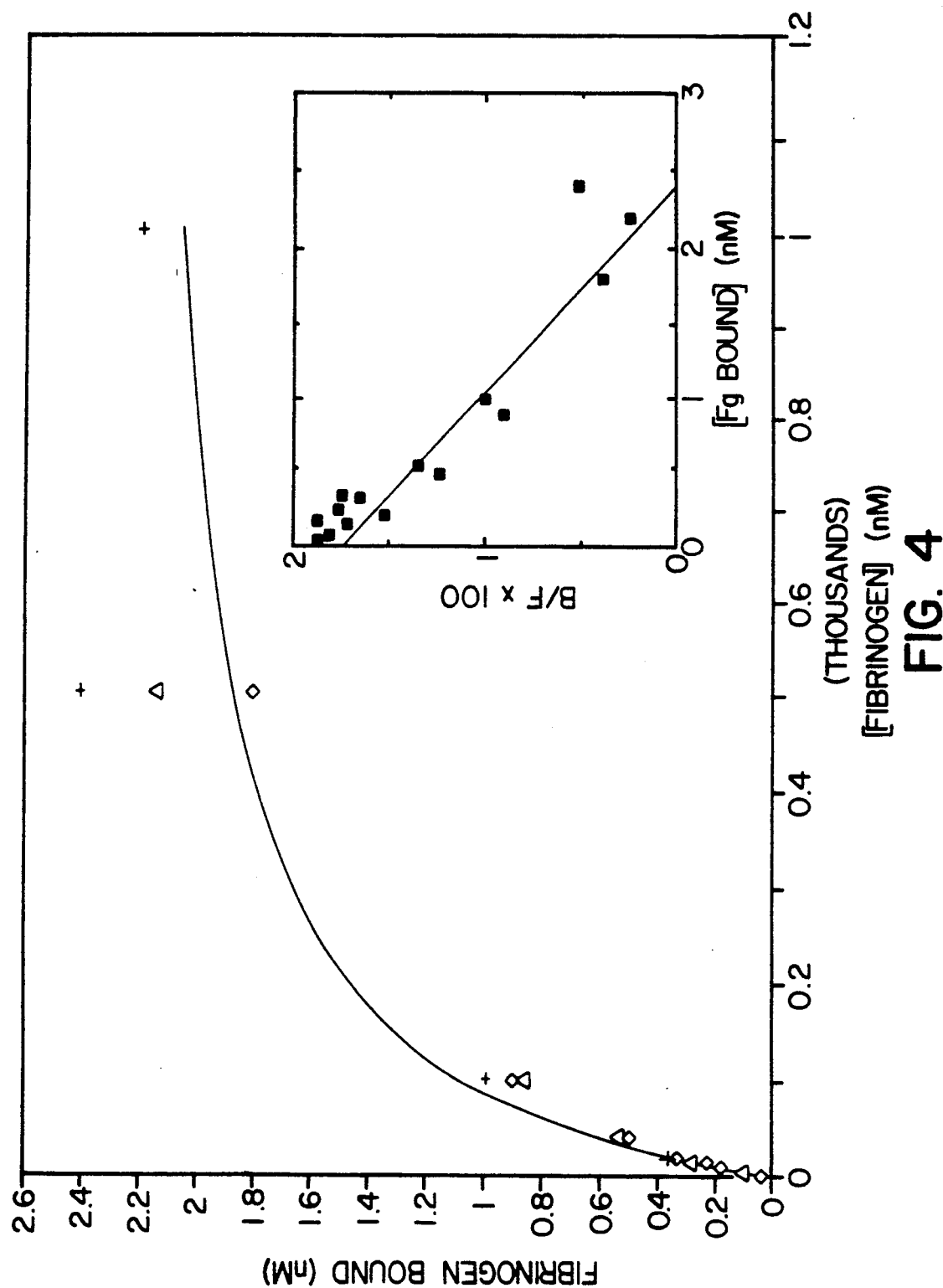
FIG. 4 illustrates the equilibrium binding of soluble fibrinogen (Fg) to Ab-62 stimulated (activated) A5 cells when measured as in Example 10. A5 cells at a concentration of $10^6$ per ml were admixed with 6 uM of Sepharose-purified AB-62 and maintained at 22 C. for 30 minutes to activate the integrin. Iodinated Fg was then admixed in varying concentrations from 0.01 to 1 nM. After a 60 minute maintenance period, the bound ligand was separated from free ligand by centrifugation through 0.3 ml of 20% sucrose. The amount of radiolabelled ligand associated with the cell pellet was determined by gamma detection. Saturable binding was measured in three different experiments and plotted versus the input Fg concentration to obtain an averaged profile. A Scatchard replot of the binding data was made and is shown in the insert.

Saturable binding was measured in three different experiments and plotted versus the input Fg concentration to obtain average data which is shown in FIG. 4. A Scatchard replot of the binding data was also made and is shown in the inset to FIG. 4. The binding of the various concentrations of Fg to activated A5 cells at steady state was analyzed by use of the "Ligand" computer program. The data were consistent with binding to a single class of sites with $K_a = 9.1 \times 10^6 35$ 1.5 $\times 10^6 M^{-1}$ (Kd = 110 nM), receptor concentration = $2.3 \pm 0.3$ nM (138,000 sites/cell), and non-saturable binding = $2.2 \pm 0.4 \times 10^{-3}$. There was day to day variation in the quantity of $\alpha_{IIb}\beta_3$ expressed as measured by the binding of the 2G12 antibody (150,000 to 440,000 sites/cell) as well as in the number of Fg receptors (138,000 to 360,000 sites/cell). The ratio of Fg receptors to $\alpha_{IIb}\beta_3$ expressed per cell on a given day was $0.83 \pm 0.05$, thus virtually all of the recombinant $\alpha_{IIb}\beta_3$ was functional with respect to Fg binding.

These results show that recombinant $\alpha_{IIb}\beta_3$ is present on the surface of CHO cells and in an unstimulated state and lacks the capacity to bind soluble Fg or PAC1, but can be activated to do so using an activating antibody of this invention. The results also show that the lack of affinity binding of these ligands to resting platelets is not due to a unique property of the platelet surface microenvironment.

11. Immunoprecipitation of Integrin

To further characterize the mode of action of the integrin-activating antibodies, the antigenic target of the antibody was identified by immunoprecipitation. A5, platelet or CHO cells were first surface labelled with $^{125}$I and cell lysates were then prepared and immunoprecipitated as described by Plow et al., *Proc. Natl. Acad. Sci. USA*, 83:6002–6006 (1986). The lysates were immunoprecipitated using P41, Ab15 or normal mouse serum (NMS), and the immunoprecipitates were analyzed on 7% polyacrylamide gels under non-reducing conditions. Labelled proteins so analyzed were then visualized by autoradiography.

Immunoprecipitation of surface labelled A5 but not CHO cells with either antibody resulted in the isolation of surface proteins with mobilities identical to $\alpha_{IIb}\beta_3$. This indicates that both antibodies bind to the recombinant $60_{IIb}\beta_3$ rather than to an endogenous CHO cell constituent.

To determine which subunit was recognized, platelet extracts and purified $\alpha_{IIb}\beta_3$ prepared in Example 1C, were immunoblotted with the same antibodies P41 or Ab15. For immunoblotting experiments, platelet lysate or purified $\alpha_{IIb}\beta_3$ were resolved on 7.5% polyacrylamide gels under non-reducing conditions and transferred to nitrocellulose. Blots were probed with specific first antibody and developed using the Vectastain ABC method (Vector Laboratories, Burlingame, Calif.). In both cases, the $\beta_3$ subunit was recognized. Thus, both monoclonal antibodies activate the receptor by binding to the $\beta_3$ subunit.

12. Activation of Integrin Occurs in the Absence of Cell Membrane

The data described in Examples 10 and 11 established that Fab fragments of the activating antibodies P41 or Ab62 activate A5 cells and platelets to express $\alpha_{IIb}\beta_3$ dependent receptors for fluid phase Fg and PAC1. To determine if this activation required intracellular signal transduction events, the capacity of these Fabs to induce PAC1 binding to formaldehyde fixed platelets was measured.

To fix platelets, blood from a normal donor was centrifuged at 1,000 rpm for 20 minutes and the resulting platelet rich plasma incubated with 2 ug/ml PGE1 and 1 mM theophylline for 15 minutes at room temperature followed by a 15 minute room temperature incubation with 0.1% paraformaldehyde. Fixed or normal platelets were then analyzed for FITC-PAC1 binding as described above in Example 9 in the presence of platelet agonists, or activating antibody P41.

Fixation of platelets completely abrogated the PAC1 response to strong agonists such as 50 nM phorbol myristate acetate (PMA) or 1 unit/ml thrombin. In sharp contrast, the response to P41 was not impaired when platelets were fixed. Both living and fixed platelets bound PACT after stimulation by P41. Thus, platelet viability was not a prerequisite for the activation response to the activating antibody.

To determine if activating antibodies could activate $\alpha_{IIb}\beta_3$ extracted away from the membrane milieu, the activating capacity to stimulate Fg binding in a solution phase was assayed. In this assay, $\alpha_{IIb}\beta_3$ was solubilized from platelets, incubated in the presence or absence of activating monoclonal antibodies, and then bound to microtiter plates coated with a non-activating monoclonal anti $\beta_3$ antibody.

Platelets were isolated as described in Example 1A and washed twice in calcium and magnesium free Tyrodes buffer (0.13 M NaCl, 0.0026 M KCl, 0.002 M $MgCl_2$—$6H_2O$, 5 mM Hepes, 0.012 m $NaHCO_3$, pH 6.5) to form a washed pellet. The platelet pellet was resuspended and solubilized in ice cold 10 mM Hepes containing 150 mM NaCl, 50 mM octyl-B-D-glucoypyranoside (Calbiochem, La Jolla, Calif.) 1 mm PMSF, 50 ng/ml PGE, 1 mM $CaCl_2$, 1 mM $MgCl_2$, 50 uM leupeptin and 1 mg/ml N-ethylmaleimide (Sigma, St. Louis, Mo.) and centrifuged at 100,000 g for 30 minutes. Platelet lysate was incubated for 15 minutes at 4 C. with 5 uM activating monoclonal antibody and then added to microtiter wells (Immunlon 2 removawell strips, Dynatech Labs, Chantilly, Va.) precoated with 15 ug/ml of the $\beta_3$ specific monoclonal antibody Mab15. The microtiter wells were incubated at 4 C. overnight, washed twice with a modified Tyrodes-Hepes buffer (2.5 mM Hepes, 150 mM NaCl, 2.5 mM KCl, 1 mM $MgCl_2$, 12 mM $NaHCO_3$, 5.5 mM D-glucose and 1 mg/ml BSA, pH 7.4) containing 50 MM octyl-B-D-glucopyranoside and 0.1 uM activating monoclonal antibody and then twice in Tyrodes-Hepes buffer only to form $\alpha_{IIb}\beta_3$-bound microtiter wells. The $\alpha_{IIb}\beta_3$-bound microtiter wells were then incubated with 50 ul of 50 nM $^{125}I$ labelled Fg (prepared as in Example 10) in the presence or absence of peptide or antibody inhibitors at room temperature for 4 hours. Bound radioactivity was counted after 2 washes with Tyrodes-Hepes buffer. In control experiments, platelet lysate was incubated in microtiter wells coated with an irrelevant antibody, TIB115, or microtiter wells coated with Mab15 were incubated with Tyrodes-Hepes lacking platelet lysate.

The results of the solution phase assay for activation of solubilized $\alpha_{IIb}\beta_3$ receptor were that only the captured receptor stimulated with either P41 or Ab62 was able to bind soluble Fg. Whereas, about 21000 cpm $^{125}I$-Fg bound per well in the absence of stimulation, representing background binding, around 11,000 cpm or 19,000 cpm of Fg bound after stimulation with P41 or Ab62, respectively. Specificity of Fg binding was verified by inhibition with cold Fg, GRGDSP peptide, and a complex specific monoclonal, 2G12. These results indicate that activation of $\alpha_{IIb}\beta_3$, and of integrins in general, can proceed in the absence of the cell membrane microenvironment.

Discussion

The major findings of the above data are: 1) Two different integrin $\alpha$ subunits ($\alpha_{IIb}$ and $\alpha_v$) form functional complexes with $\beta$ subunits encoded by the same MRNA and the $\alpha$ subunit regulates peptide ligand recognition specificity; 2) While stable $\alpha_{IIb}\beta_3$ transfectants are unable to bind avidly soluble Fg or the activation specific monoclonal, PAC1, when stimulated with certain anti-$\beta_3$ monoclonal antibodies, namely activating anti-$\beta_3$ monoclonal antibodies, they do express these binding functions; 3) Activation of $\alpha_{IIb}\beta_3$ with these antibodies can proceed in the absence of signal transduction events or a cell membrane. Thus, $\alpha_{IIb}\beta_3$ activation is not an inherent property of platelets or their microenvironment, but is an intrinsic property of the receptor itself.

Based on partial sequence identity, immunological cross reactivity and similar electrophoretic migration [Ginsberg et al., *J. Biol. Chem.*, 262:5437–5440 (1987)], the $\beta$ subunits associated with $\alpha_{IIb}$ and $\alpha_v$ have been assumed to be identical or highly similar. The $\beta_3$ clone used herein was isolated from an endothelial cell library, is probably the $\beta$ subunit of $\alpha_v\beta_3$, and formed heterodimers with either $\alpha_v$ or $\alpha_{IIb}$. Each recombinant heterodimer retained its characteristic antigenic specificity and had relative affinities for synthetic peptides similar to those of the native receptor but different from each other. Since they share a $\beta$ subunit coded by the same mRNA, the different peptide recognition specificities of the recombinant $\beta_3$ integrins are attributable to the $\alpha$ subunit. In particular, the fibrinogen $gamma_{402-411}$ (L10) peptide was recognized better by $\alpha_{IIb}\beta_3$ than by $\alpha_v\beta_3$. The 21 residues spanning $\alpha_{IIb}$ 294–314 are proximal to or part of the binding site for a peptide containing $gamma_{402-411}$ and show significant sequence divergence from the similar region of $\alpha_v$ [D'Sousa et al., *J. Biol. Chem.*, 265:3440–3446 (1990)]. Thus, this region of the $\alpha$ subunit contributes to the difference in peptide ligand recognition specificity.

Recombinant $\alpha_{IIb}\beta_3$ stably expressed in CHO cells is functionally similar to that in resting platelet, with respect to antigenic, peptide, and insoluble macromolecule $\alpha_{IIb}\beta_3$ ligand binding properties. Recombinant $\alpha_{IIb}\beta_3$ is expressed in an inactive state as it fails to bind avidly Fg and the activation specific monoclonal PAC1 while it supports cell adhesion to immobilized Fg. Recombinant $\alpha_{IIb}\beta_3$ does possess the potential capacity to bind fluid phase macromolecules since stimulation with activating anti-$\beta_3$ monoclonal antibodies resulted in specific binding of PAC1 or Fg. These activating antibodies are effective on both recombinant and native $\alpha_{IIb}\beta_3$ and exert their effect by acting directly on the receptor based on 3 lines of evidence. First, Fab fragments of P41 and Ab62 were effective activators. Thus, these antibodies do not depend on their Fc fragment to mediate this effect. This is in contrast to platelet activation by certain anti CD9 antibodies which do utilize the Fc region of the activating antibody. See, for example, Jennings et al., *J Biol. Chem.*, 265:3815-3822 (1990); Worthington et al., *Br. J. Haematol.*, 74:216-222 (1990); Boucheix et al., *FEBS Lett.*, 161:289-295 (1983). The efficacy of the Fab fragments to activate also suggests that receptor crosslinking by antibody is not critical in the activation mechanism. Secondly, these antibodies stimulate PAC1 binding under conditions where strong agonists are unable to activate platelets. Thus, activation by these antibodies does not appear to require signal transduction events, or living cells. This is in contrast to other agonists, which generally require living, actively metabolizing cells. Finally, P41 and Ab62 are able to stimulate soluble Fg binding to solubilized $\alpha_{IIb}\beta_3$ isolated from platelet membranes. Activation, therefore, is an inherent property of the receptor itself and does not invariably require signal transduction or a cell membrane. The most likely explanation of the antibody effect is alteration of receptor conformation, allowing it to bind fluid phase macromolecules with higher affinity.

Platelet $\alpha_{IIb}\beta$ is a prototype of the role activation plays in affinity modulation of integrins. It is clear that other integrin subfamilies also require activation for full functional competence. stimulation of Mac-I ($\alpha_M\beta_2$) and LFA1 ($\alpha_L\beta_2$) with agents such as phorbol esters, ADP, or N-formyl peptides promotes in vitro neutrophil aggregation or lymphocyte adhesion [Wright et al., J. Immunol., 136:1759-1764 (1986); Detmers et al., J. Cell Biol., 105:1137-1145 (1987)] as well as high affinity binding of fluid phase Fg [Altieri et al., J. Cell Biol., 107:1893-1900 (1988)]. Activation of these receptors appears not to require recruitment of new surface receptors, but rather involved a modification of existing receptors [Phillips et al., J. Clin. Invest., 82:495-501 (1988); Buyon et al., J. Immunol., 140:3156-3160 (1988)].

The above data demonstrate that affinity modulation controls the functional activity of integrins. since the affinity of integrins for specific ligands controls cellular migration, invasiveness, cytoskeletal organization and adhesion [Hynes Cell, 48:549-554 (1987)], the activating anti-$\beta_3$ antibodies described here are useful to modulate these cellular functions in an integrin and adhesive ligand specific manner.

The foregoing specification, including the specific embodiments and Examples, is intended to be illustrative of the present invention and is not to be taken as limiting. Numerous other variations and modifications can be effected without departing from the true spirit and scope of the present invention.

What is claimed is:

1. A diagnostic method for determining activation competence of viable cells having cell surface integrin comprising:
    (a) admixing said cells in a physiological fluid with an activating amount of integrin-activating antibodies that:
        (i) immunoreact with said integrin and when immunoreacted increase the binding affinity of said integrin for binding to its specific ligand; and
        (ii) immunoreact with a ligand-induced binding site formed on said integrin when said integrin is specifically bound to said specific ligand, to form an activating admixture;
    (b) maintaining said activating admixture for a time period sufficient for said cell surface integrin to immunoreact with said integrin-activating antibodies and form an activated integrin immunocomplex on the surface of said cells; and
    (c) assaying for the presence of said activated integrin immunocomplex formed in step (b) and thereby the activation competence of said cell,
    wherein said integrin is GPIIb-IIIa, and said integrin-activating antibodies immunoreact with the GPIIIa subunit.

2. The method of claim 1 wherein said presence of said activated integrin immunocomplex is assayed by:
    (i) admixing said activated integrin immunocomplex with an activation-specific ligand that specifically binds with activated integrin but does not specifically bind with resting integrin to form a binding admixture;
    (ii) maintaining said binding admixture for a predetermined time period sufficient for said activation-specific ligand to bind to said activated integrin immunocomplex that is present in said binding admixture and form a binding reaction product; and
    (iii) detecting said binding reaction product formed in step (ii) and thereby the presence of activated integrin immunocomplex.

3. The diagnostic method of claim 1 wherein said cells are platelets.

4. The diagnostic method of claim 1 wherein said integrin-activating antibodies are secreted by hybridoma PMI-2, HB9615.

UNITED STATES PATENT AND TRADEMARK OFFICE
CERTIFICATE OF CORRECTION

PATENT NO. : 5,306,620
DATED : April 26, 1994
INVENTOR(S) : Mark H. Ginsberg et al.

It is certified that error appears in the above-identified patent and that said Letters Patent is hereby corrected as shown below:

Column 1,
Line 6, insert -- This invention was made with government support under Grant Nos. HL 39150, HL 23235 and HL 16411 by the National Institutes of Health. The government has certain rights in the invention. --

Signed and Sealed this

Twenty-first Day of May, 2002

*Attest:*

*Attesting Officer*

JAMES E. ROGAN
*Director of the United States Patent and Trademark Office*